US012653673B2

(12) United States Patent
Wei et al.

(10) Patent No.: US 12,653,673 B2
(45) Date of Patent: Jun. 16, 2026

(54) ANNULAR AUGMENTATION DEVICE FOR CARDIAC VALVE REPAIR

(71) Applicant: EVALVE, INC., Santa Clara, CA (US)

(72) Inventors: Michael F. Wei, Redwood City, CA (US); Chad J. Abunassar, San Francisco, CA (US)

(73) Assignee: EVALVE, INC., Santa Clara, CA (US)

( * ) Notice: Subject to any disclaimer, the term of this patent is extended or adjusted under 35 U.S.C. 154(b) by 1292 days.

(21) Appl. No.: 17/200,379

(22) Filed: Mar. 12, 2021

(65) Prior Publication Data

US 2021/0196454 A1 Jul. 1, 2021

Related U.S. Application Data

(63) Continuation of application No. 15/629,505, filed on Jun. 21, 2017, now Pat. No. 10,945,842.

(Continued)

(51) Int. Cl.
*A61F 2/24* (2006.01)

(52) U.S. Cl.
CPC ............ *A61F 2/246* (2013.01); *A61F 2/2454* (2013.01); *A61F 2/2463* (2013.01);
(Continued)

(58) Field of Classification Search
CPC .................... A61F 2/246; A61F 2/2463; A61F 2220/0008; A61F 2220/0016;
(Continued)

(56) References Cited

U.S. PATENT DOCUMENTS

| 2,097,018 A | 10/1937 | Chamberlin |
| 2,108,206 A | 2/1938 | Meeker |

(Continued)

FOREIGN PATENT DOCUMENTS

| CA | 2296317 C | 1/2009 |
| CN | 1142351 A | 2/1997 |

(Continued)

OTHER PUBLICATIONS

Abe et al."De Vega's annuloplasty for acquired tricuspid disease: Early and late results in 110 patients" Ann. Thorac. Surg. (1989) 48:670-676.

(Continued)

*Primary Examiner* — Thomas C Barrett
*Assistant Examiner* — Teresa M Dudden
(74) *Attorney, Agent, or Firm* — SLEMAN & LUND LLP

(57) ABSTRACT

The present disclosure relates to repair devices for repair of regurgitant mitral valves. A repair device includes a body having a perimeter defining an upper side and a lower side. An annular groove is disposed along a posterior section of the perimeter of the device and is configured to receive posterior rim tissue of a mitral valve annulus. First and second anchors extend from the body in an anterior direction. The first and second anchors are configured to engage with respective commissures of the mitral valve to assist in securing the repair device in position. The repair device is structured to minimize or eliminate imparting or transmitting radially outward forces along an anterior section so as to avoid imparting forces to the septum to avoid hindering the function of the aortic valve and the left ventricular outflow tract.

19 Claims, 10 Drawing Sheets

Related U.S. Application Data

(60) Provisional application No. 62/371,080, filed on Aug. 4, 2016.

(52) U.S. Cl.
CPC .... *A61F 2/2466* (2013.01); *A61F 2210/0014* (2013.01); *A61F 2210/0076* (2013.01); *A61F 2220/0008* (2013.01); *A61F 2220/0016* (2013.01); *A61F 2230/0013* (2013.01); *A61F 2240/001* (2013.01); *A61F 2250/0098* (2013.01)

(58) Field of Classification Search
CPC .............. A61F 2230/0013; A61F 2/243; A61F 2/2454; A61F 2/24
See application file for complete search history.

(56) References Cited

U.S. PATENT DOCUMENTS

| | | |
|---|---|---|
| 3,296,668 A | 1/1967 | Aiken |
| 3,378,010 A | 4/1968 | Codling |
| 3,557,780 A | 1/1971 | Sato |
| 3,671,979 A | 6/1972 | Moulopoulos |
| 3,675,639 A | 7/1972 | Cimber |
| 3,874,338 A | 4/1975 | Happel |
| 3,874,388 A | 4/1975 | King |
| 4,007,743 A | 2/1977 | Blake |
| 4,055,861 A | 11/1977 | Carpentier |
| 4,056,854 A | 11/1977 | Boretos |
| 4,064,881 A | 12/1977 | Meredith |
| 4,091,815 A | 5/1978 | Larsen |
| 4,112,951 A | 9/1978 | Hulka |
| 4,235,238 A | 11/1980 | Ogiu |
| 4,297,749 A | 11/1981 | Davis |
| 4,327,736 A | 5/1982 | Inoue |
| 4,340,091 A | 7/1982 | Skelton |
| 4,425,908 A | 1/1984 | Simon |
| 4,458,682 A | 7/1984 | Cerwin |
| 4,484,579 A | 11/1984 | Meno |
| 4,487,205 A | 12/1984 | Di Giovanni |
| 4,498,476 A | 2/1985 | Cerwin |
| 4,510,934 A | 4/1985 | Batra |
| 4,531,522 A | 7/1985 | Bedi |
| 4,578,061 A | 3/1986 | Lemelson |
| 4,641,366 A | 2/1987 | Yokoyama |
| 4,657,024 A | 4/1987 | Coneys |
| 4,686,965 A | 8/1987 | Bonnet |
| 4,693,248 A | 9/1987 | Failla |
| 4,716,886 A | 1/1988 | Schulman |
| 4,777,951 A | 10/1988 | Cribier |
| 4,795,458 A | 1/1989 | Regan |
| 4,809,695 A | 3/1989 | Gwathmey |
| 4,917,089 A | 4/1990 | Sideris |
| 4,930,674 A | 6/1990 | Barak |
| 4,944,295 A | 7/1990 | Gwathmey |
| 4,969,890 A | 11/1990 | Sugita |
| 4,994,077 A | 2/1991 | Dobben |
| 5,002,562 A | 3/1991 | Oberlander |
| 5,015,249 A | 5/1991 | Nakao |
| 5,019,096 A | 5/1991 | Fox, Jr. |
| 5,042,707 A | 8/1991 | Taheri |
| 5,047,041 A | 9/1991 | Samuels |
| 5,049,153 A | 9/1991 | Nakao |
| 5,061,277 A | 10/1991 | Carpentier |
| 5,069,679 A | 12/1991 | Taheri |
| 5,098,440 A | 3/1992 | Hillstead |
| 5,108,368 A | 4/1992 | Hammerslag |
| 5,125,758 A | 6/1992 | Dewan |
| 5,125,895 A | 6/1992 | Buchbinder |
| 5,147,370 A | 9/1992 | Mcnamara |
| 5,171,252 A | 12/1992 | Friedland |
| 5,171,259 A | 12/1992 | Inoue |
| 5,190,554 A | 3/1993 | Coddington, III |
| 5,195,968 A | 3/1993 | Lundquist |
| 5,209,756 A | 5/1993 | Seedhom |
| 5,222,963 A | 6/1993 | Brinkerhoff |
| 5,226,429 A | 7/1993 | Kuzmak |
| 5,226,911 A | 7/1993 | Chee |
| 5,234,437 A | 8/1993 | Sepetka |
| 5,242,456 A | 9/1993 | Nash |
| 5,250,071 A | 10/1993 | Palermo |
| 5,251,611 A | 10/1993 | Zehel |
| 5,254,130 A | 10/1993 | Poncet |
| 5,261,916 A | 11/1993 | Engelson |
| 5,271,381 A | 12/1993 | Ailinger |
| 5,271,544 A | 12/1993 | Fox |
| 5,275,578 A | 1/1994 | Adams |
| 5,282,845 A | 2/1994 | Bush |
| 5,304,131 A | 4/1994 | Paskar |
| 5,306,283 A | 4/1994 | Conners |
| 5,306,286 A | 4/1994 | Stack |
| 5,312,415 A | 5/1994 | Palermo |
| 5,314,424 A | 5/1994 | Nicholas |
| 5,318,525 A | 6/1994 | West |
| 5,320,632 A | 6/1994 | Heidmueller |
| 5,325,845 A | 7/1994 | Adair |
| 5,327,905 A | 7/1994 | Avitall |
| 5,330,442 A | 7/1994 | Green |
| 5,330,501 A | 7/1994 | Tovey |
| 5,332,402 A | 7/1994 | Teitelbaum |
| 5,334,217 A | 8/1994 | Das |
| 5,342,393 A | 8/1994 | Stack |
| 5,350,397 A | 9/1994 | Palermo |
| 5,350,399 A | 9/1994 | Erlebacher |
| 5,359,994 A | 11/1994 | Krauter |
| 5,363,861 A | 11/1994 | Edwards |
| 5,368,564 A | 11/1994 | Savage |
| 5,368,601 A | 11/1994 | Sauer |
| 5,383,886 A | 1/1995 | Kensey |
| 5,389,077 A | 2/1995 | Melinyshyn |
| 5,391,182 A | 2/1995 | Chin |
| 5,403,312 A | 4/1995 | Yates |
| 5,403,326 A | 4/1995 | Harrison |
| 5,411,552 A | 5/1995 | Andersen |
| 5,413,584 A | 5/1995 | Schulze |
| 5,417,699 A | 5/1995 | Klein |
| 5,417,700 A | 5/1995 | Egan |
| 5,423,857 A | 6/1995 | Rosenman |
| 5,423,858 A | 6/1995 | Bolanos |
| 5,423,882 A | 6/1995 | Jackman |
| 5,425,744 A | 6/1995 | Fagan |
| 5,431,666 A | 7/1995 | Sauer |
| 5,437,551 A | 8/1995 | Chalifoux |
| 5,437,681 A | 8/1995 | Meade |
| 5,447,966 A | 9/1995 | Hermes |
| 5,450,860 A | 9/1995 | O'Connor |
| 5,452,837 A | 9/1995 | Williamson, IV |
| 5,456,400 A | 10/1995 | Shichman |
| 5,456,674 A | 10/1995 | Bos |
| 5,456,684 A | 10/1995 | Schmidt |
| 5,462,527 A | 10/1995 | Stevens-Wright |
| 5,472,044 A | 12/1995 | Hall |
| 5,476,470 A | 12/1995 | Fitzgibbons, Jr. |
| 5,477,856 A | 12/1995 | Lundquist |
| 5,478,309 A | 12/1995 | Sweezer |
| 5,478,353 A | 12/1995 | Yoon |
| 5,487,746 A | 1/1996 | Yu |
| 5,496,332 A | 3/1996 | Sierra |
| 5,507,725 A | 4/1996 | Savage |
| 5,507,755 A | 4/1996 | Gresl |
| 5,507,757 A | 4/1996 | Sauer |
| 5,520,701 A | 5/1996 | Lerch |
| 5,522,873 A | 6/1996 | Jackman |
| 5,527,313 A | 6/1996 | Scott |
| 5,527,321 A | 6/1996 | Hinchliffe |
| 5,527,322 A | 6/1996 | Klein |
| 5,536,251 A | 7/1996 | Evard |
| 5,540,705 A | 7/1996 | Meade |
| 5,542,949 A | 8/1996 | Yoon |
| 5,554,185 A | 9/1996 | Block |
| 5,562,678 A | 10/1996 | Booker |
| 5,569,274 A | 10/1996 | Rapacki |
| 5,571,085 A | 11/1996 | Accisano, III |

(56)                References Cited

U.S. PATENT DOCUMENTS

| | | | |
|---|---|---|---|
| 5,571,137 | A | 11/1996 | Marlow |
| 5,571,215 | A | 11/1996 | Sterman |
| 5,575,802 | A | 11/1996 | McQuilkin |
| 5,582,611 | A | 12/1996 | Tsuruta |
| 5,593,424 | A | 1/1997 | Northrup III |
| 5,593,435 | A | 1/1997 | Carpentier |
| 5,601,224 | A | 2/1997 | Bishop |
| 5,601,574 | A | 2/1997 | Stefanchik |
| 5,607,462 | A | 3/1997 | Imran |
| 5,607,471 | A | 3/1997 | Seguin |
| 5,609,598 | A | 3/1997 | Laufer |
| 5,611,794 | A | 3/1997 | Sauer |
| 5,618,306 | A | 4/1997 | Roth |
| 5,620,452 | A | 4/1997 | Yoon |
| 5,620,461 | A | 4/1997 | Muijs Van De Moer |
| 5,626,588 | A | 5/1997 | Sauer |
| 5,634,932 | A | 6/1997 | Schmidt |
| 5,636,634 | A | 6/1997 | Kordis |
| 5,639,277 | A | 6/1997 | Mariant |
| 5,640,955 | A | 6/1997 | Ockuly |
| 5,649,937 | A | 7/1997 | Bito |
| 5,662,681 | A | 9/1997 | Nash |
| 5,669,917 | A | 9/1997 | Sauer |
| 5,690,671 | A | 11/1997 | McGurk |
| 5,695,504 | A | 12/1997 | Gifford, III |
| 5,695,505 | A | 12/1997 | Yoon |
| 5,702,825 | A | 12/1997 | Keita |
| 5,706,824 | A | 1/1998 | Whittier |
| 5,709,707 | A | 1/1998 | Lock |
| 5,713,910 | A | 2/1998 | Gordon |
| 5,713,911 | A | 2/1998 | Racenet |
| 5,715,817 | A | 2/1998 | Stevens-Wright |
| 5,716,367 | A | 2/1998 | Koike |
| 5,716,417 | A | 2/1998 | Girard |
| 5,718,725 | A | 2/1998 | Sterman |
| 5,719,725 | A | 2/1998 | Nakao |
| 5,722,421 | A | 3/1998 | Francese |
| 5,725,542 | A | 3/1998 | Yoon |
| 5,725,556 | A | 3/1998 | Moser |
| 5,738,649 | A | 4/1998 | Macoviak |
| 5,741,280 | A | 4/1998 | Fleenor |
| 5,741,297 | A | 4/1998 | Simon |
| 5,749,828 | A | 5/1998 | Yeung |
| 5,755,778 | A | 5/1998 | Kleshinski |
| 5,759,193 | A | 6/1998 | Burbank |
| 5,769,812 | A | 6/1998 | Stevens |
| 5,769,863 | A | 6/1998 | Garrison |
| 5,772,578 | A | 6/1998 | Heimberger |
| 5,782,239 | A | 7/1998 | Webster, Jr. |
| 5,782,845 | A | 7/1998 | Shewchuk |
| 5,797,927 | A | 8/1998 | Yoon |
| 5,797,960 | A | 8/1998 | Stevens |
| 5,810,847 | A | 9/1998 | Laufer |
| 5,810,849 | A | 9/1998 | Kontos |
| 5,810,853 | A | 9/1998 | Yoon |
| 5,810,876 | A | 9/1998 | Kelleher |
| 5,814,029 | A | 9/1998 | Hassett |
| 5,814,097 | A | 9/1998 | Sterman |
| 5,820,592 | A | 10/1998 | Hammerslag |
| 5,820,631 | A | 10/1998 | Nobles |
| 5,823,955 | A | 10/1998 | Kuck |
| 5,823,956 | A | 10/1998 | Roth |
| 5,824,065 | A | 10/1998 | Gross |
| 5,827,237 | A | 10/1998 | Macoviak |
| 5,829,447 | A | 11/1998 | Stevens |
| 5,833,671 | A | 11/1998 | Macoviak |
| 5,836,955 | A | 11/1998 | Buelna |
| 5,840,081 | A | 11/1998 | Andersen |
| 5,843,031 | A | 12/1998 | Hermann |
| 5,843,178 | A | 12/1998 | Vanney |
| 5,849,019 | A | 12/1998 | Yoon |
| 5,853,422 | A | 12/1998 | Huebsch |
| 5,855,271 | A | 1/1999 | Eubanks |
| 5,855,590 | A | 1/1999 | Malecki |
| 5,855,601 | A | 1/1999 | Bessler |
| 5,855,614 | A | 1/1999 | Stevens |
| 5,860,990 | A | 1/1999 | Nobles |
| 5,861,003 | A | 1/1999 | Latson |
| 5,868,733 | A | 2/1999 | Ockuly |
| 5,876,399 | A | 3/1999 | Chia |
| 5,879,307 | A | 3/1999 | Chio |
| 5,885,271 | A | 3/1999 | Hamilton |
| 5,891,160 | A | 4/1999 | Williamson, IV |
| 5,916,147 | A | 6/1999 | Boury |
| 5,928,224 | A | 7/1999 | Laufer |
| 5,944,733 | A | 8/1999 | Engelson |
| 5,947,363 | A | 9/1999 | Bolduc |
| 5,954,732 | A | 9/1999 | Hart |
| 5,957,949 | A | 9/1999 | Leonhardt |
| 5,972,020 | A | 10/1999 | Carpentier |
| 5,972,030 | A | 10/1999 | Garrison |
| 5,976,159 | A | 11/1999 | Bolduc |
| 5,980,455 | A | 11/1999 | Daniel |
| 5,989,284 | A | 11/1999 | Laufer |
| 6,015,417 | A | 1/2000 | Reynolds, Jr. |
| 6,017,358 | A | 1/2000 | Yoon |
| 6,019,722 | A | 2/2000 | Spence |
| 6,022,360 | A | 2/2000 | Reimels |
| 6,033,378 | A | 3/2000 | Lundquist |
| 6,036,699 | A | 3/2000 | Andreas |
| 6,045,497 | A | 4/2000 | Schweich, Jr. |
| 6,048,351 | A | 4/2000 | Gordon |
| 6,056,769 | A | 5/2000 | Epstein |
| 6,059,757 | A | 5/2000 | Macoviak |
| 6,060,628 | A | 5/2000 | Aoyama |
| 6,060,629 | A | 5/2000 | Pham |
| 6,063,106 | A | 5/2000 | Gibson |
| 6,066,146 | A | 5/2000 | Carroll |
| 6,066,856 | A | 5/2000 | Fishman |
| 6,068,628 | A | 5/2000 | Fanton |
| 6,068,629 | A | 5/2000 | Haissaguerre |
| 6,077,214 | A | 6/2000 | Mortier |
| 6,079,414 | A | 6/2000 | Roth |
| 6,086,600 | A | 7/2000 | Kortenbach |
| 6,088,889 | A | 7/2000 | Luther |
| 6,099,505 | A | 8/2000 | Ryan |
| 6,099,553 | A | 8/2000 | Hart |
| 6,110,145 | A | 8/2000 | Macoviak |
| 6,117,144 | A | 9/2000 | Nobles |
| 6,117,159 | A | 9/2000 | Huebsch |
| 6,120,496 | A | 9/2000 | Whayne |
| 6,123,699 | A | 9/2000 | Webster, Jr. |
| 6,126,658 | A | 10/2000 | Baker |
| 6,132,447 | A | 10/2000 | Dorsey |
| 6,136,010 | A | 10/2000 | Modesitt |
| 6,143,024 | A | 11/2000 | Campbell |
| 6,149,658 | A | 11/2000 | Gardiner |
| 6,159,240 | A | 12/2000 | Sparer |
| 6,162,233 | A | 12/2000 | Williamson, IV |
| 6,165,164 | A | 12/2000 | Hill |
| 6,165,183 | A | 12/2000 | Kuehn |
| 6,165,204 | A | 12/2000 | Levinson |
| 6,168,614 | B1 | 1/2001 | Andersen |
| 6,171,320 | B1 | 1/2001 | Monassevitch |
| 6,182,664 | B1 | 2/2001 | Cosgrove |
| 6,187,003 | B1 | 2/2001 | Buysse |
| 6,190,408 | B1 | 2/2001 | Melvin |
| 6,193,734 | B1 | 2/2001 | Bolduc |
| 6,200,315 | B1 | 3/2001 | Gaiser |
| 6,203,531 | B1 | 3/2001 | Ockuly |
| 6,203,553 | B1 | 3/2001 | Robertson |
| 6,206,893 | B1 | 3/2001 | Klein |
| 6,206,907 | B1 | 3/2001 | Marino |
| 6,210,419 | B1 | 4/2001 | Mayenberger |
| 6,210,432 | B1 | 4/2001 | Solem |
| 6,217,528 | B1 | 4/2001 | Koblish |
| 6,245,079 | B1 | 6/2001 | Nobles |
| 6,258,021 | B1 | 7/2001 | Wilk |
| 6,267,746 | B1 | 7/2001 | Bumbalough |
| 6,267,781 | B1 | 7/2001 | Tu |
| 6,269,534 | B1 | 8/2001 | Mattmann |
| 6,269,819 | B1 | 8/2001 | Oz |
| 6,277,555 | B1 | 8/2001 | Duran |
| 6,283,127 | B1 | 9/2001 | Sterman |

(56) References Cited

U.S. PATENT DOCUMENTS

| | | |
|---|---|---|
| 6,283,962 B1 | 9/2001 | Tu |
| 6,290,674 B1 | 9/2001 | Roue |
| 6,299,637 B1 | 10/2001 | Shaolian |
| 6,306,133 B1 | 10/2001 | Tu |
| 6,312,447 B1 | 11/2001 | Grimes |
| 6,319,250 B1 | 11/2001 | Falwell |
| 6,322,559 B1 | 11/2001 | Daulton |
| 6,332,880 B1 | 12/2001 | Yang |
| 6,332,893 B1 | 12/2001 | Mortier |
| 6,346,074 B1 | 2/2002 | Roth |
| 6,352,708 B1 | 3/2002 | Duran |
| 6,355,030 B1 | 3/2002 | Aldrich |
| 6,358,277 B1 | 3/2002 | Duran |
| 6,368,326 B1 | 4/2002 | Dakin |
| 6,387,104 B1 | 5/2002 | Pugsley, Jr. |
| 6,402,780 B2 | 6/2002 | Williamson, IV |
| 6,402,781 B1 | 6/2002 | Langberg |
| 6,406,420 B1 | 6/2002 | McCarthy |
| 6,419,669 B1 | 7/2002 | Frazier |
| 6,419,695 B1 | 7/2002 | Gabbay |
| 6,419,696 B1 | 7/2002 | Ortiz |
| 6,461,366 B1 | 10/2002 | Seguin |
| 6,464,707 B1 | 10/2002 | Bjerken |
| 6,482,224 B1 | 11/2002 | Michler |
| 6,485,489 B2 | 11/2002 | Teirstein |
| 6,508,828 B1 | 1/2003 | Akerfeldt |
| 6,533,796 B1 | 3/2003 | Sauer |
| 6,537,314 B2 | 3/2003 | Langberg |
| 6,540,755 B2 | 4/2003 | Ockuly |
| 6,544,215 B1 | 4/2003 | Bencini |
| 6,551,303 B1 | 4/2003 | Van Tassel |
| 6,551,331 B2 | 4/2003 | Nobles |
| 6,562,037 B2 | 5/2003 | Paton |
| 6,562,052 B2 | 5/2003 | Nobles |
| 6,575,971 B2 | 6/2003 | Hauck |
| 6,585,761 B2 | 7/2003 | Taheri |
| 6,599,311 B1 | 7/2003 | Biggs |
| 6,616,684 B1 | 9/2003 | Mdlund |
| 6,619,291 B2 | 9/2003 | Hlavka |
| 6,626,899 B2 | 9/2003 | Houser |
| 6,626,930 B1 | 9/2003 | Allen |
| 6,629,534 B1 | 10/2003 | Frederick |
| 6,641,592 B1 | 11/2003 | Sauer |
| 6,656,221 B2 | 12/2003 | Taylor |
| 6,669,687 B1 | 12/2003 | Saadat |
| 6,685,648 B2 | 2/2004 | Flaherty |
| 6,689,164 B1 | 2/2004 | Seguin |
| 6,695,866 B1 | 2/2004 | Kuehn |
| 6,701,929 B2 | 3/2004 | Hussein |
| 6,702,825 B2 | 3/2004 | Frazier |
| 6,702,826 B2 | 3/2004 | Liddicoat |
| 6,709,382 B1 | 3/2004 | Horner |
| 6,709,456 B2 | 3/2004 | Langberg |
| 6,718,985 B2 | 4/2004 | Hlavka |
| 6,719,767 B1 | 4/2004 | Kimblad |
| 6,723,038 B1 | 4/2004 | Schroeder |
| 6,726,716 B2 | 4/2004 | Marquez |
| 6,740,107 B2 | 5/2004 | Loeb |
| 6,746,471 B2 | 6/2004 | Mortier |
| 6,752,813 B2 | 6/2004 | Goldfarb |
| 6,755,777 B2 | 6/2004 | Schweich, Jr. |
| 6,764,510 B2 | 7/2004 | Vidlund |
| 6,767,349 B2 | 7/2004 | Ouchi |
| 6,770,083 B2 | 8/2004 | Seguin |
| 6,797,001 B2 | 9/2004 | Mathis |
| 6,797,002 B2 | 9/2004 | Spence |
| 6,837,867 B2 | 1/2005 | Kortelling |
| 6,855,137 B2 | 2/2005 | Bon |
| 6,860,179 B2 | 3/2005 | Hopper |
| 6,875,224 B2 | 4/2005 | Grimes |
| 6,908,481 B2 | 6/2005 | Cribier |
| 6,926,715 B1 | 8/2005 | Hauck |
| 6,926,730 B1 | 8/2005 | Nguyen |
| 6,945,978 B1 | 9/2005 | Hyde |
| 6,949,122 B2 | 9/2005 | Adams |
| 6,966,914 B2 | 11/2005 | Abe |
| 6,986,775 B2 | 1/2006 | Morales |
| 7,004,970 B2 | 2/2006 | Cauthen III |
| 7,011,669 B2 | 3/2006 | Kimblad |
| 7,048,754 B2 | 5/2006 | Martin |
| 7,101,395 B2 | 9/2006 | Tremulis |
| 7,112,207 B2 | 9/2006 | Allen |
| 7,125,421 B2 | 10/2006 | Tremulis |
| 7,160,322 B2 | 1/2007 | Gabbay |
| 7,166,127 B2 | 1/2007 | Spence |
| 7,226,467 B2 | 6/2007 | Lucatero |
| 7,288,097 B2 | 10/2007 | Seguin |
| 7,297,144 B2 | 11/2007 | Fleischman |
| 7,381,210 B2 | 6/2008 | Zarbatany |
| 7,404,824 B1 | 7/2008 | Webler |
| 7,431,726 B2 | 10/2008 | Spence |
| 7,464,712 B2 | 12/2008 | Oz |
| 7,497,822 B1 | 3/2009 | Kugler |
| 7,533,790 B1 | 5/2009 | Knodel |
| 7,563,267 B2 | 7/2009 | Goldfarb |
| 7,563,273 B2 | 7/2009 | Goldfarb |
| 7,569,062 B1 | 8/2009 | Kuehn |
| 7,604,646 B2 | 10/2009 | Goldfarb |
| 7,635,329 B2 | 12/2009 | Goldfarb |
| 7,651,502 B2 | 1/2010 | Jackson |
| 7,655,015 B2 | 2/2010 | Goldfarb |
| 7,678,145 B2 | 3/2010 | Vidlund |
| 7,704,269 B2 | 4/2010 | St. Goar |
| 7,798,953 B1 | 9/2010 | Wilk |
| 7,811,296 B2 | 10/2010 | Goldfarb |
| 7,927,370 B2 | 4/2011 | Webler |
| 7,972,323 B1 | 7/2011 | Bencini |
| 8,062,313 B2 | 11/2011 | Kimblad |
| 8,118,822 B2 | 2/2012 | Schaller |
| 8,142,495 B2 | 3/2012 | Hasenkam |
| 2001/0004715 A1 | 6/2001 | Duran |
| 2001/0005787 A1 | 6/2001 | Oz |
| 2001/0010005 A1 | 7/2001 | Kammerer |
| 2001/0018611 A1 | 8/2001 | Solem |
| 2001/0022872 A1 | 9/2001 | Marui |
| 2001/0037084 A1 | 11/2001 | Nardeo |
| 2001/0039411 A1 | 11/2001 | Johansson |
| 2001/0044568 A1 | 11/2001 | Langberg |
| 2002/0013571 A1 | 1/2002 | Goldfarb |
| 2002/0022848 A1 | 2/2002 | Garrison |
| 2002/0026233 A1 | 2/2002 | Shaknovich |
| 2002/0035361 A1 | 3/2002 | Houser |
| 2002/0035381 A1 | 3/2002 | Bardy |
| 2002/0042651 A1 | 4/2002 | Liddicoat |
| 2002/0055767 A1 | 5/2002 | Forde |
| 2002/0055774 A1 | 5/2002 | Liddicoat |
| 2002/0055775 A1 | 5/2002 | Carpentier |
| 2002/0058910 A1 | 5/2002 | Hermann |
| 2002/0058995 A1 | 5/2002 | Stevens |
| 2002/0077687 A1 | 6/2002 | Ahn |
| 2002/0087148 A1 | 7/2002 | Brock |
| 2002/0087169 A1 | 7/2002 | Brock |
| 2002/0087173 A1 | 7/2002 | Alferness |
| 2002/0103532 A1 | 8/2002 | Langberg |
| 2002/0107534 A1 | 8/2002 | Schaefer |
| 2002/0147456 A1 | 10/2002 | Diduch |
| 2002/0156526 A1 | 10/2002 | Hlavka |
| 2002/0158528 A1 | 10/2002 | Tsuzaki |
| 2002/0161378 A1 | 10/2002 | Downing |
| 2002/0169360 A1 | 11/2002 | Taylor |
| 2002/0183766 A1 | 12/2002 | Seguin |
| 2002/0183787 A1 | 12/2002 | Wahr |
| 2002/0183835 A1 | 12/2002 | Taylor |
| 2003/0005797 A1 | 1/2003 | Hopper |
| 2003/0045778 A1 | 3/2003 | Ohline |
| 2003/0050693 A1 | 3/2003 | Quijano |
| 2003/0069570 A1 | 4/2003 | Witzel |
| 2003/0069593 A1 | 4/2003 | Tremulis |
| 2003/0069636 A1 | 4/2003 | Solem |
| 2003/0074012 A1 | 4/2003 | Nguyen |
| 2003/0078654 A1 | 4/2003 | Taylor |
| 2003/0083742 A1 | 5/2003 | Spence |
| 2003/0105519 A1 | 6/2003 | Fasol |
| 2003/0105520 A1 | 6/2003 | Alferness |

(56) References Cited

U.S. PATENT DOCUMENTS

| | | | |
|---|---|---|---|
| 2003/0120340 A1 | 6/2003 | Liska | |
| 2003/0120341 A1 | 6/2003 | Shennib | |
| 2003/0130669 A1 | 7/2003 | Damarati | |
| 2003/0130730 A1 | 7/2003 | Cohn | |
| 2003/0130731 A1 | 7/2003 | Mdlund | |
| 2003/0144697 A1 | 7/2003 | Mathis | |
| 2003/0167071 A1 | 9/2003 | Martin | |
| 2003/0171776 A1 | 9/2003 | Adams | |
| 2003/0187467 A1 | 10/2003 | Schreck | |
| 2003/0195562 A1 | 10/2003 | Collier | |
| 2003/0199975 A1* | 10/2003 | Gabbay | A61F 2/2454 |
| | | | 623/1.14 |
| 2003/0208231 A1 | 11/2003 | Williamson | |
| 2003/0229395 A1 | 12/2003 | Cox | |
| 2003/0233038 A1 | 12/2003 | Hassett | |
| 2004/0002719 A1 | 1/2004 | Oz | |
| 2004/0003819 A1 | 1/2004 | St. Goar | |
| 2004/0019377 A1 | 1/2004 | Taylor | |
| 2004/0019378 A1 | 1/2004 | Hlavka | |
| 2004/0024414 A1 | 2/2004 | Downing | |
| 2004/0030382 A1 | 2/2004 | St. Goar | |
| 2004/0034365 A1 | 2/2004 | Lentz | |
| 2004/0039442 A1 | 2/2004 | St. Goar | |
| 2004/0039443 A1 | 2/2004 | Solem | |
| 2004/0044350 A1 | 3/2004 | Martin | |
| 2004/0044365 A1 | 3/2004 | Bachman | |
| 2004/0049207 A1 | 3/2004 | Goldfarb | |
| 2004/0049211 A1 | 3/2004 | Tremulis | |
| 2004/0073302 A1 | 4/2004 | Rourke | |
| 2004/0078053 A1 | 4/2004 | Berg | |
| 2004/0087975 A1 | 5/2004 | Lucatero | |
| 2004/0088047 A1 | 5/2004 | Spence | |
| 2004/0092962 A1 | 5/2004 | Thornton | |
| 2004/0097878 A1 | 5/2004 | Anderson | |
| 2004/0097979 A1 | 5/2004 | Svanidze | |
| 2004/0106989 A1 | 6/2004 | Wilson | |
| 2004/0111099 A1 | 6/2004 | Nguyen | |
| 2004/0122448 A1 | 6/2004 | Levine | |
| 2004/0127981 A1 | 7/2004 | Rahdert | |
| 2004/0127982 A1 | 7/2004 | Machold | |
| 2004/0127983 A1 | 7/2004 | Mortier | |
| 2004/0133062 A1 | 7/2004 | Pai | |
| 2004/0133063 A1 | 7/2004 | McCarthy | |
| 2004/0133082 A1 | 7/2004 | Abraham-Fuchs | |
| 2004/0133192 A1 | 7/2004 | Houser | |
| 2004/0133220 A1 | 7/2004 | Lashinski | |
| 2004/0133240 A1 | 7/2004 | Adams | |
| 2004/0133273 A1 | 7/2004 | Cox | |
| 2004/0138744 A1 | 7/2004 | Lashinski | |
| 2004/0138745 A1 | 7/2004 | Macoviak | |
| 2004/0143323 A1 | 7/2004 | Chawla | |
| 2004/0148021 A1 | 7/2004 | Cartledge | |
| 2004/0152847 A1 | 8/2004 | Emri | |
| 2004/0152947 A1 | 8/2004 | Schroeder | |
| 2004/0153144 A1 | 8/2004 | Seguin | |
| 2004/0158123 A1 | 8/2004 | Jayaraman | |
| 2004/0162610 A1 | 8/2004 | Liska | |
| 2004/0167539 A1 | 8/2004 | Kuehn | |
| 2004/0186486 A1 | 9/2004 | Roue | |
| 2004/0186566 A1 | 9/2004 | Hindrichs | |
| 2004/0193191 A1 | 9/2004 | Starksen | |
| 2004/0215339 A1 | 10/2004 | Drasler | |
| 2004/0220593 A1* | 11/2004 | Greenhalgh | A61F 2/246 |
| | | | 606/151 |
| 2004/0220657 A1 | 11/2004 | Nieminen | |
| 2004/0225300 A1 | 11/2004 | Goldfarb | |
| 2004/0236354 A1 | 11/2004 | Seguin | |
| 2004/0243229 A1 | 12/2004 | Mdlund | |
| 2004/0249452 A1 | 12/2004 | Adams | |
| 2004/0249453 A1 | 12/2004 | Cartledge | |
| 2004/0260393 A1 | 12/2004 | Rahdert | |
| 2005/0004583 A1 | 1/2005 | Oz | |
| 2005/0004665 A1 | 1/2005 | Aklog | |
| 2005/0004668 A1* | 1/2005 | Aklog | A61F 2/2448 |
| | | | 623/2.36 |
| 2005/0021056 A1 | 1/2005 | St. Goar | |
| 2005/0021057 A1 | 1/2005 | St. Goar | |
| 2005/0021058 A1 | 1/2005 | Negro | |
| 2005/0033446 A1 | 2/2005 | Deem | |
| 2005/0038508 A1 | 2/2005 | Gabbay | |
| 2005/0038509 A1 | 2/2005 | Ashe | |
| 2005/0049698 A1 | 3/2005 | Bolling | |
| 2005/0055089 A1 | 3/2005 | Macoviak | |
| 2005/0059351 A1 | 3/2005 | Cauwels | |
| 2005/0119734 A1 | 6/2005 | Spence | |
| 2005/0119735 A1 | 6/2005 | Spence | |
| 2005/0125011 A1 | 6/2005 | Spence | |
| 2005/0137700 A1 | 6/2005 | Spence | |
| 2005/0148815 A1 | 7/2005 | Mortier | |
| 2005/0149014 A1 | 7/2005 | Hauck | |
| 2005/0159810 A1 | 7/2005 | Filsoufi | |
| 2005/0177180 A1 | 8/2005 | Kaganov | |
| 2005/0197694 A1 | 9/2005 | Pai | |
| 2005/0197695 A1 | 9/2005 | Stacchino | |
| 2005/0216039 A1 | 9/2005 | Lederman | |
| 2005/0228422 A1* | 10/2005 | Machold | A61B 17/0401 |
| | | | 606/167 |
| 2005/0228495 A1 | 10/2005 | Macoviak | |
| 2005/0251001 A1 | 11/2005 | Hassett | |
| 2005/0267493 A1 | 12/2005 | Schreck | |
| 2005/0267571 A1 | 12/2005 | Spence | |
| 2005/0273160 A1 | 12/2005 | Lashinski | |
| 2005/0277966 A1 | 12/2005 | Ewers | |
| 2005/0287493 A1 | 12/2005 | Novak | |
| 2006/0004247 A1 | 1/2006 | Kute | |
| 2006/0015003 A1 | 1/2006 | Moaddes | |
| 2006/0020275 A1 | 1/2006 | Goldfarb | |
| 2006/0030866 A1 | 2/2006 | Schreck | |
| 2006/0030867 A1 | 2/2006 | Zadno | |
| 2006/0030885 A1 | 2/2006 | Hyde | |
| 2006/0058871 A1 | 3/2006 | Zakay | |
| 2006/0064115 A1 | 3/2006 | Allen | |
| 2006/0064116 A1 | 3/2006 | Allen | |
| 2006/0064118 A1 | 3/2006 | Kimblad | |
| 2006/0069429 A1 | 3/2006 | Spence | |
| 2006/0089671 A1 | 4/2006 | Goldfarb | |
| 2006/0089711 A1 | 4/2006 | Dolan | |
| 2006/0135993 A1 | 6/2006 | Seguin | |
| 2006/0178700 A1 | 8/2006 | Quinn | |
| 2006/0184203 A1 | 8/2006 | Martin | |
| 2006/0195012 A1 | 8/2006 | Mortier | |
| 2006/0195183 A1 | 8/2006 | Navia | |
| 2006/0229708 A1 | 10/2006 | Powell | |
| 2006/0241745 A1 | 10/2006 | Solem | |
| 2006/0252984 A1 | 11/2006 | Rahdert | |
| 2006/0287716 A1 | 12/2006 | Banbury | |
| 2007/0038293 A1 | 2/2007 | St. Goar | |
| 2007/0080188 A1 | 4/2007 | Spence | |
| 2007/0093890 A1 | 4/2007 | Eliasen | |
| 2007/0100356 A1 | 5/2007 | Lucatero | |
| 2007/0112424 A1 | 5/2007 | Spence | |
| 2007/0118151 A1 | 5/2007 | Davidson | |
| 2007/0118154 A1 | 5/2007 | Crabtree | |
| 2007/0118155 A1 | 5/2007 | Goldfarb | |
| 2007/0129737 A1 | 6/2007 | Goldfarb | |
| 2007/0198082 A1 | 8/2007 | Kapadia | |
| 2007/0293943 A1 | 12/2007 | Quinn | |
| 2008/0039935 A1 | 2/2008 | Buch | |
| 2008/0051703 A1 | 2/2008 | Thornton | |
| 2008/0051807 A1 | 2/2008 | St. Goar | |
| 2008/0097489 A1 | 4/2008 | Goldfarb | |
| 2008/0125860 A1 | 5/2008 | Webler | |
| 2008/0125861 A1 | 5/2008 | Webler | |
| 2008/0167714 A1 | 7/2008 | St. Goar | |
| 2008/0183194 A1 | 7/2008 | Goldfarb | |
| 2008/0228223 A1 | 9/2008 | Alkhatib | |
| 2008/0275503 A1 | 11/2008 | Spence | |
| 2008/0288061 A1 | 11/2008 | Maurer | |
| 2008/0319541 A1 | 12/2008 | Filsoufi | |
| 2009/0043381 A1 | 2/2009 | Macoviak | |
| 2009/0043382 A1 | 2/2009 | Maurer | |
| 2009/0048668 A1 | 2/2009 | Wilson | |
| 2009/0149949 A1 | 6/2009 | Quinn | |
| 2009/0156995 A1 | 6/2009 | Martin | |

(56) References Cited

U.S. PATENT DOCUMENTS

| | | | |
|---|---|---|---|
| 2009/0163934 A1 | 6/2009 | Raschdorf, Jr. | |
| 2009/0177266 A1 | 7/2009 | Powell | |
| 2009/0198322 A1 | 8/2009 | Deem | |
| 2009/0270858 A1 | 10/2009 | Hauck | |
| 2009/0326567 A1 | 12/2009 | Goldfarb | |
| 2010/0016958 A1 | 1/2010 | St. Goar | |
| 2010/0022823 A1 | 1/2010 | Goldfarb | |
| 2010/0100108 A1 | 4/2010 | Goldfarb | |
| 2010/0185276 A1 | 7/2010 | Vidlund | |
| 2010/0318184 A1 | 12/2010 | Spence | |
| 2010/0324585 A1 | 12/2010 | Miles | |
| 2011/0029071 A1 | 2/2011 | Zlotnick | |
| 2011/0077733 A1 | 3/2011 | Solem | |
| 2011/0224784 A1 | 9/2011 | Quinn | |
| 2011/0288626 A1* | 11/2011 | Straubinger | A61F 2/2427 623/2.11 |
| 2012/0078358 A1 | 3/2012 | Vidlund | |
| 2012/0197388 A1* | 8/2012 | Khairkhahan | A61B 17/064 623/2.11 |
| 2013/0090728 A1 | 4/2013 | Solem | |
| 2015/0100116 A1* | 4/2015 | Mohl | A61F 2/2454 623/2.11 |
| 2015/0119981 A1 | 4/2015 | Khairkhahan et al. | |
| 2016/0045314 A1 | 2/2016 | Keren et al. | |
| 2018/0250132 A1 | 9/2018 | Ketai | |
| 2019/0350710 A1 | 11/2019 | Ketai | |

FOREIGN PATENT DOCUMENTS

| | | | |
|---|---|---|---|
| DE | 10116168 A1 | 11/2001 | |
| EP | 0179562 B1 | 7/1989 | |
| EP | 0684012 A2 | 11/1995 | |
| EP | 0727239 A2 | 8/1996 | |
| EP | 0782836 A1 | 7/1997 | |
| EP | 0558031 B1 | 4/1999 | |
| EP | 1230899 A1 | 8/2002 | |
| EP | 1383448 A2 | 1/2004 | |
| EP | 1674040 A2 | 6/2006 | |
| EP | 1752115 A1 | 2/2007 | |
| GB | 1598111 A | 9/1981 | |
| GB | 2151142 A | 7/1985 | |
| JP | H09192137 | 7/1997 | |
| JP | 09253030 A | 9/1997 | |
| JP | 11089937 A | 4/1999 | |
| JP | 2000283130 A | 10/2000 | |
| JP | 5985653 B2 | 9/2016 | |
| WO | 8100668 A1 | 3/1981 | |
| WO | 9101689 A1 | 2/1991 | |
| WO | 9118881 A1 | 12/1991 | |
| WO | 9212690 A1 | 8/1992 | |
| WO | 9418881 A1 | 9/1994 | |
| WO | 94018893 A1 | 9/1994 | |
| WO | 9511620 A2 | 5/1995 | |
| WO | 9515715 A1 | 6/1995 | |
| WO | 9614032 A1 | 5/1996 | |
| WO | 9620655 A1 | 7/1996 | |
| WO | 9622735 A1 | 8/1996 | |
| WO | 9630072 A1 | 10/1996 | |
| WO | 9632882 A1 | 10/1996 | |
| WO | 9718746 A2 | 5/1997 | |
| WO | 9725927 A1 | 7/1997 | |
| WO | 9726034 A1 | 7/1997 | |
| WO | 9727807 A1 | 8/1997 | |
| WO | 9738748 A2 | 10/1997 | |
| WO | 9739688 A2 | 10/1997 | |
| WO | 9748436 A2 | 12/1997 | |
| WO | 9807375 A1 | 2/1998 | |
| WO | 9824372 A1 | 6/1998 | |
| WO | 9830153 A1 | 7/1998 | |
| WO | 9832382 A1 | 7/1998 | |
| WO | 9835638 A1 | 8/1998 | |
| WO | 9900059 A1 | 1/1999 | |
| WO | 9901377 A1 | 1/1999 | |
| WO | 9907354 A2 | 2/1999 | |
| WO | 9913777 A1 | 3/1999 | |
| WO | 9915223 A1 | 4/1999 | |
| WO | 9966967 A1 | 12/1999 | |
| WO | 0002489 A1 | 1/2000 | |
| WO | 0003651 A1 | 1/2000 | |
| WO | 0003759 A2 | 1/2000 | |
| WO | 0012168 A1 | 3/2000 | |
| WO | 0044313 A1 | 8/2000 | |
| WO | 0059382 A1 | 10/2000 | |
| WO | 0060995 A2 | 10/2000 | |
| WO | 0100111 A1 | 1/2001 | |
| WO | 0100114 A1 | 1/2001 | |
| WO | 0103651 A2 | 1/2001 | |
| WO | 0126557 A1 | 4/2001 | |
| WO | 0126586 A1 | 4/2001 | |
| WO | 0126587 A1 | 4/2001 | |
| WO | 0126588 A2 | 4/2001 | |
| WO | 0126703 A1 | 4/2001 | |
| WO | 0128432 A1 | 4/2001 | |
| WO | 0128455 A1 | 4/2001 | |
| WO | 0135832 A2 | 5/2001 | |
| WO | 0147438 A1 | 7/2001 | |
| WO | 0149213 A2 | 7/2001 | |
| WO | 0150985 A1 | 7/2001 | |
| WO | 0154618 A1 | 8/2001 | |
| WO | 0156512 A1 | 8/2001 | |
| WO | 0166001 A2 | 9/2001 | |
| WO | 0170320 A1 | 9/2001 | |
| WO | 0189440 A2 | 11/2001 | |
| WO | 0195831 A2 | 12/2001 | |
| WO | 0195832 A2 | 12/2001 | |
| WO | 0197741 A2 | 12/2001 | |
| WO | 0200099 A2 | 1/2002 | |
| WO | 0201999 A2 | 1/2002 | |
| WO | 0203892 A1 | 1/2002 | |
| WO | 2002034167 A2 | 5/2002 | |
| WO | 02060352 A1 | 8/2002 | |
| WO | 02062263 A2 | 8/2002 | |
| WO | 02062270 A1 | 8/2002 | |
| WO | 02062408 A2 | 8/2002 | |
| WO | 02085251 | 10/2002 | |
| WO | 03001893 A2 | 1/2003 | |
| WO | 03003930 A1 | 1/2003 | |
| WO | 03020179 A1 | 3/2003 | |
| WO | 03028558 A2 | 4/2003 | |
| WO | 03037171 A2 | 5/2003 | |
| WO | 03047467 A1 | 6/2003 | |
| WO | 03049619 A2 | 6/2003 | |
| WO | 03073910 A2 | 9/2003 | |
| WO | 03073913 A2 | 9/2003 | |
| WO | 03082129 A2 | 10/2003 | |
| WO | 03105667 A2 | 12/2003 | |
| WO | 2004004607 A1 | 1/2004 | |
| WO | 2004012583 A1 | 2/2004 | |
| WO | 2004012583 A2 | 2/2004 | |
| WO | 2004012789 A1 | 2/2004 | |
| WO | 2004012789 A2 | 2/2004 | |
| WO | 2004014282 A2 | 2/2004 | |
| WO | 2004019811 A2 | 3/2004 | |
| WO | 2004030568 A2 | 4/2004 | |
| WO | 2004030570 A2 | 4/2004 | |
| WO | 2004037317 A2 | 5/2004 | |
| WO | 2004045370 A2 | 6/2004 | |
| WO | 2004045378 A2 | 6/2004 | |
| WO | 2004045463 A2 | 6/2004 | |
| WO | 2004047679 A1 | 6/2004 | |
| WO | 2004047679 A2 | 6/2004 | |
| WO | 2004062725 A1 | 7/2004 | |
| WO | 2004082523 A2 | 9/2004 | |
| WO | 2004082538 A2 | 9/2004 | |
| WO | 2004089250 A1 | 10/2004 | |
| WO | 2004093730 A2 | 11/2004 | |
| WO | 2004103162 A2 | 12/2004 | |
| WO | 2004112585 A2 | 12/2004 | |
| WO | 2004112651 A2 | 12/2004 | |
| WO | 2005002424 A2 | 1/2005 | |
| WO | 2005018507 A2 | 3/2005 | |
| WO | 2005027797 A1 | 3/2005 | |
| WO | 2005032421 A2 | 4/2005 | |

(56) References Cited

FOREIGN PATENT DOCUMENTS

| WO | 2005062391 | | 7/2005 |
|----|------------|------|---------|
| WO | 2005062931 | A2 | 7/2005 |
| WO | 2005112792 | A2 | 12/2005 |
| WO | 2006019520 | | 2/2006 |
| WO | 2006019521 | A2 | 2/2006 |
| WO | 2006041877 | A2 | 4/2006 |
| WO | 06086434 | A1 | 8/2006 |
| WO | 2006086434 | | 8/2006 |
| WO | 2006105008 | A1 | 10/2006 |
| WO | 2006105009 | A1 | 10/2006 |
| WO | 06116558 | A2 | 11/2006 |
| WO | 2006115875 | A2 | 11/2006 |
| WO | 2006115876 | A2 | 11/2006 |
| WO | 2006116558 | | 11/2006 |
| WO | 2006127509 | A2 | 11/2006 |
| WO | 2007100268 | | 9/2007 |
| WO | 2008141322 | A2 | 11/2008 |
| WO | 2009064998 | A1 | 5/2009 |
| WO | 2009072114 | A2 | 6/2009 |
| WO | 2010128502 | A1 | 11/2010 |
| WO | WO/2015/020971 | | 2/2015 |

OTHER PUBLICATIONS

Abe et al."Updated: De Vega's annuloplasty for acquired tricuspid disease: Early and late results in 110 patients" Ann. Thorac. Surg. (1996) 62:1876-1877.

Agricola et al., "Mitral valve reserve in double orifice technique: an exercise echocardiographic study," Journal of Heart Valve Disease(2002)11(5):637 643.

Alfieri et al., "An effective technique to correct anterior mitral leaflet prolapse," J Card Surg(1999) 14(6):468-470.

Alfieri et al., "Novel suture device for beating heart mitral leaflet approximation," Annals of Thoracic Surgery(2002) 74:1488 1493.

Alfieri et al., "The double orifice technique in mitral valve repair: a simple solution for complex problems," Journal of Thoracic Cardiovascular Surgery(2001)122:674 681.

Alfieri, "The edge-to-edge repair of the mitral valve," [Abstract] 6th Annual NewEra Cardiac Care: Innovation & Tecnology, Heart Surgery Forum(2003) p. 103.

Alvarez et al., "Repairing the degenerative mitral valve: Ten- to fifteen-year follow-up" J. Thorac. Cardiovasc. Surg. (1996) 112:238-247.

Arisi et al., "Mitral valve repair with Alfieri technique in mitral regurgitation of diverse etiology: early echocardiographic results," Circulation Supplement II(2001) 104(17):3240.

Arthur C. Beall et al., Clinical Experience with a Dacron Velour-Covered Teflon-Disc Mitral Valve Prosthesis, 5 Ann. Thorac. Surg. 402-10 (1968).

Bach et al., "Early improvement in congestive heart failure after correction of secondary mitral regurgitation in end-stage cardiomyopathy," Am. Heart J.(1995) 129:1165-1170.

Bach et al., "Improvement following correction of secondary mitral regurgitation in end-stage cardiomyopathy with mitral annuloplasty" Am. J. Cardiol.(1996) 78:966-969.

Bailey, "Surgery of the Heart," Chapter 20(1995) pp. 686-737.

Bernal et al."The 'Valve Racket': a new and different concept of atrioventricular valve repair," Eur. J. Cardio-thoracic Surgery 29:1026-29 (2006).

Bhudia et al., "Edge-to-edge (Alfieri) mitral repair: results in diverse clinical settings," Ann Thorac Surg, 77: 1598-1606 (2004).

Bolling et al., Surgery for Acquired Heart Disease: Early Outcome of Mitral Valve Reconstruction in Patients with End-stage Cardiomyopathy, J. Thor. and Cariovasc. Surg., Apr. 1995, pp. 676-683, vol. 109.

Borghetti et al., "Preliminary observations on haemodynamics during physiological stress conditions following 'double-orifice' mitral valve repair," European Journal of Cardio-thoracic Surgery, Apr. 18(2001) 20:262-269.

Castedo, "Edge-to-Edge Tricuspid Repair for Redeveloped Valve Incompetence after DeVega's Annuloplasty," Ann Thora Surg., 75:605-606 (2003).

Copelan, "How Dr. Oz Kick-Started a Groundbreaking Device for Patients with Heart Failure," Parade (Sep. 26, 2018).

Cribier et al., "Percutaneous Mechanical Mitral Commissurotomy With a Newly Designed Metallic Valvulotome: Immediate Results of the Initial Experience in 153 Patients," Circulation 99:793-799 (1999).

Cribier, A., et al., "Percutaneous Mitral Valvotomy with a Metal Dilatator," The Lancet 349:1667 (1997).

Dec et al., "Idiopathic dilated cardiomyopathy," N. Engl. J. Med. (1994) 331:1564-1575. 12 pages.

Dias de Azeredo Bastos et al., "Percutaneous Mechanical Mitral Commissurotomy Performed With a Cribier's Metallic Valvulotome. Initial Results," Arq Bras Cardiol, 77:126-131 (2001).

Dottori et al., "Echocardiographic imaging of the Alfieri type mitral valve repair," Ital Heart J(2001) 2(4):319-320.

Downing et al., "Beating heart mitral valve surgery: Preliminary model and methodology," Journal of Thoracic and Cardiovascular Surgery(2002) 123(6):1141-1146.

Falk et al., "Computer-Enhanced Mitral Valve Surgery: Toward a Total Endoscopic Procedure," Seminars in Thoracic and Cardiovascular Surgery, 11(3):244-249 (1999).

Feldman, T., et al., "Technique of Percutaneous Transvenous Mitral Commissurotomy Using the Inoue Balloon Catheter," Catheterization and Cardiovascular Diagnosis Supplement 2:26-34 (1994).

Filsoufi et al. "Restoring Optimal Surface of Coaptation With a Mini Leaflet Prosthesis: A New Surgical Concept for the Correction of Mitral Velve Prolapse," Int'l. Soc. for Minimally Invasive Cardiothoracic Surgery 1(4):186-87 (2006).

Frazier et al., #62 Early Clinical Experience With An Implantable, Intracardiac Circulatory Support Device: Operative Considerations and Physiologic Implications, 2003 STS Presentation1 page total. [Abstract Only].

Freeny et al., "Subselective Diagnostic and Interventional Arteriography Using a Simple Coaxial Catheter System," Cardiovasc. Intervent. Radiol. 7:209-213 (1984).

Fucci et al., Improved Results with Mitral Valve Repair Using New Surgical Techniques, Eur. J. Cardiothorac. Surg., Nov. 1995, pp. 621-627, vol. 9.

Fundaro et al., "Chordal plication and free edge remodeling for mitral anterior leaflet prolapse repair: 8-year follow-up," Annals of Thoracic Surgery(2001) 72:1515-1519.

Garcia-Rinaldi et al., "Left ventricular volume reduction and reconstruction is ischemic cardiomyopathy," Journal of Cardiac Surgery(1999) 14:199-210.

Gateliene, "Early and postoperative results results of metal and tricuspid valve insufficiency surgical treatment using edge-to-edge central coaptation procedure," Medicina 38 (Suppl 2): 172-175 (2002) [Article in LithuanianEnglish summary on p. 174 of the article].

Gatti et al."The edge to edge technique as a trick to rescue an imperfect mitral valve repair," Eur J Cardiothorac Surg. (2002) 22(5):817 20.

Gillinov et al., "Is Minimally Invasive Heart Valve Surgery a Paradigm for the Future?" Current Cardiology Reports, 1:318-322 (1999).

Glazier, J. and Turi, Z., "Percutaneous Balloon Mitral Valvuloplasty," Progress in Cardiovascular Diseases 40(1):5-26 (1997).

Gregg W. Stone et al., Clinical Trial Design Principles and Endpoint Definitions for Transcatheter Mitral Valve Repair and Replacement: Part 1: Clinical Trial Design Principles: A Consensus Document from the Mitral Valve Academic Research Consortium, 66 J. Am. Coll. Cardiol. 278-307 (2015).

Gundry et al., "Facile Mitral Valve Repair Utilizing Leaflet Edge Approximation: Midterm Results of the Alfieri Figure of Eight Repair," The Western Thoracic Surgical Association, Scientific Session (May 1999). 1 page.

Gupta et al., #61 Influence of Older Donor Grafts on Heart Transplant Survival: Lack of Recipient Effects, 2003 STS Presentation[Abstract Only]. 1 page.

(56)             References Cited

OTHER PUBLICATIONS

Hung et al., "Atrial Septal Puncture Technique in Percutaneous Transvenous Mitral Commissurotomy : Mitral Valvuloplasty Using the Inoue Balloon Catheter Technique," Catheterization and Cardiovascular Diagnosis 26: 275-284 (1992).

Hung et al., "Pitfalls and Tips in Inoue Balloon Mitral Commissurotomy," Catheterization and Cardiovascular Diagnosis, 37:188-199 (1996).

Ikeda et al., "Batista's operation with coronary artery bypass grafting and mitral valve plasty for ischemic dilated cardiomyopathy," The Japanese Journal of Thoracic and Cardiovascular Surgery(2000) 48:746-749.

Ing et al., "The Snare-Assisted Technique for Transcatheter Coil Occlusion of Moderate to Large Patent Ductus Arteriosus: Immediate and Intermediate Results," J. Am. Col. Cardiol. 33(6):1710-1718 (1999).

Inoue, K. and Feldman, T., "Percutaneous Transvenous Mitral Commissurotomy Using the Inoue Balloon Catheter," Catheterization and Cardiovascular Diagnosis 28:119-125 (1993).

Inoue, K., et al., "Clinical Application of Transvenous Mitral Commissurotomy by a New Balloon Catheter," J Thorac Cardiovasc Surg 87:394-402 (1984).

Izzat et al., "Early experience with partial left ventriculectomy in the Asia-Pacific Region," Annuals of Thoracic Surgery (1999) 67:1703-1707.

Källner et al., "Transaortic approach for the Alfieri Stitch," Ann Thorac Surg(2001) 71:378-380.

Kameda et al., Annuloplasty for Severe Mitral Regurgitation Due to Dilated Cardiomyopathy, Ann. Thorac. Surg., 1996, pp. 1829-1832, vol. 61.

Kavarana et al., "Transaortic Repair of Mitral Regurgitation," The Heart Surgery Forum, #2000-2389, 3(1):24-28 (2000).

Kaza et al., "Ventricular Reconstruction Results in Improved Left Ventricular Function and Amelioration of Mitral Insufficiency," Annals of Surgery, 235(6):828-832 (2002).

Khan et al., "Blade atrial septostomy: Experience with the first 50 procedures" Cathet. Cardiovasc. Diagn(1991)23:257-262.

Kherani et al., "Edge-to-edge mitral valve repair: the Columbia Presbyterian experience," Ann Thorac Surg2004; 78:73-76.

Konertz et at, "Results after partial left ventriculectomy in a European heart failure population," Journal of Cardiac Surgery(1999) 14(2):129-135.

Kron et al., "Surgical relocation of the posterior papillary muscle in chronic ischemic mitral regurgitation," Annals. of Thoracic Surgery(2002)74:600 601.

Krüger et al., "Edge to edge technique in complex mitral valve repair," Thorac Cardiovasc Surg, (2000) Thema: Posterhttp://www.thieme.de/thoracic/abstracts/abstracts/p-73.html.

Langer et al."Posterior mitral leaflet extensions: An adjunctive repair option for ischemic mitral regurgitation?," J. Thorac. Cardiovasc. Surf. 131:868-77 (2006).

Lau, K. and Hung, J., "'Balloon Impasse'; A Marker for Severe Mitral Subvalvular Disease and a Predictor of Mitral Regurgitation in Inoue-Balloon Percutaneous Transvenous Mitral Commissurotomy," Catheterization and Cardiovascular Diagnosis 35:310-319 (1995).

Lock et al., "Transcatheter Closure of Atrial Septal Defects: Experimental Studies," Circulation 79:1091-1099 (1989).

Lorusso et al., "Double-Orifice" technique to repair extensive mitral valve excision following acute endocarditis, J Card Surg(1998) 13:24-26.

Lorusso et al., "The double-orifice technique for mitral valve construction: predictors of postoperative outcome," Eur J. Cardiothorac Surg(2001) 20(3):583-589.

Maisano et al., "The double orifice repair for Barlow Disease: a simple solution for a complex repair," Supplement I Circulation(1999) 100(18):I-94.

Maisano et al., "The double orifice technique as a standardized approach to treat mitral regurgitation due to severe myxomatous disease: surgical technique," European Journal of Cardiothoracic Surgery(2000) 17:201-215.

Maisano et al., "The edge-to-edge technique: A simplified method to correct mitral insufficiency" Eur. J. Cardiothorac. Surg.(1998) 13:240-246.

Maisano et al., "The hemodynamic effects of double-orifice valve repair for mitral regurgitation: a 3D computational model," European Journal of Cardio-thoracic Surgery(1999) 15:419-425.

Maisano et al., "Valve repair for traumatic tricuspid regurgitation," Eur J. Cardio-thorac Surg(1996) 10:867-873.

Mantovani et al., "Edge-to-edge repair of congenital familiar tricuspid regurgitation: case report," J. Heart Valve Dis. (2000) 9 (5):641-643.

McCarthy and Cosgrove et al."Tricuspid Valve Reapir with the Cosgrove- Edwards Annuloplasty System," Ann. Thorac. Surg. 64:267-268 (1997).

McCarthy et al., "Partial left ventriculectomy and mitral valve repair for end-stage congestive heart failure," European Journal of Cardio-thoracic Surgery(1998) 13:337-343.

McCarthy, P., et al., "Early Results with Partial Left Ventriculectomy," J Thorac Cardiovasc Surg 114(5):755-765 (1997).

Moainie et al., Correction of traumatic tricuspid regurgitation using the double orifice technique, Annals of Thoracic Surgery(2002) 73:963 965.

Morales et al., "Development of an off bypass mitral valve repair," The Heart Surgery Forum #1999-4963(1999) 2(2):115-120.

Netter, F. H., et al., "The Ciba Collection of Medical Illustrations," vol. 5. Royal Victorian Institute for the Blind Tertiary Resource Service, Melbourne (1969).

Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. I):I-29-I-35 (2001).

Noera et al.. , "Tricuspid Valve Incompetence Caused by Nonpenetrating Thoracic Trauma", Annals of Thoracic Surgery, 1991, 51 (2)320-322.

O'Rourke, R. and Crawford, M., "Mitral Valve Regurgitation," Year Book Medical Publishers, Inc. 1-52 (1984).

Osawa et al., "Partial Left Ventriculectomy in a 3-Year Old Boy with Dilated Cardiomyopathy," Japanese Journal of Thoracic and Cardiovascular Surg, 48:590-593 (2000).

Otto, Catherine M., "Timing of Surgery in Mitral Regurgitation," Heart 89:100-105 (2003).

Park et al. "Clinical use of a blade atrial septostomy" Circulation (1978) 58:600-608.

Patel et al., #57 Epicardial Atrial Defibrillation: Novel Treatment Of Postoperative Atrial Fibrillation, 2003 STS Presentation[Abstract Only]. 1 page.

Privitera et al."Mitral Valve Repair: Clinical Outcome and Pathology; Circulation," (2002) 106:173.

Rahhal, "Tiny device to 'zip up' leaky hearts invented by Dr Oz 20 years ago could save millions, study finds," Daily Mail (Sep. 26, 2018).

Randas J. V. Batista et al., Partial Left Ventriculectomy to Treat End-Stage Heart Disease, 64 Ann. Thorac. Surg. 634-38 (1997).

Redaelli et al., "A Computational Study of the Hemodynamics After 'Edge-To-Edge' Mitral Valve Repair," Journal of Biomechanical Engineering, 123:565-570 (2001).

Reul, "Mital valve reconstruction for mitral insufficiency," Progress in Cardiovascular Diseases, (1997) vol. XXXIX, No. 6pp. 567-599.

Ricchi et al., Linear Segmental Annuloplasty for Mitral Valve Repair, Ann. Thorac. Surg., Jan. 7, 1997, pp. 1805-1806, vol. 63.

Robicsek et al., #60 The Bicuspid Aortic Valve: How Does It Function? Why Does It Fail?, 2003 STS Presentation [Abstract Only]. 1 page.

Tager et al., Long-Term Follow-Up of Rheumatic Patients Undergoing Left-Sided Valve Replacement With Tricuspid Annuloplasty— Validity of Preoperative Echocardiographic Criteria in the Decision to Perform Tricuspid Annuloplasty, Am. J. Cardiol., Apr. 15, 1998, pp. 1013-1016, vol. 81.

(56) References Cited

OTHER PUBLICATIONS

Tamura et al., "Edge to Edge Repair for Mitral Regurgitation in a Patient with Chronic Hemodialysis: Report of a Case," Kyobu Geka. The Japanese Journal of Thoracic Surgery, 54(9):788-790 (2001).

Tibayan et al., #59 Annular Geometric Remodeling In Chronic Ischemic Mitral Regurgitation, 2003 STS Presentation [Abstract Only]. 2 pages.

Timek, "Edge-to-edge mitral repair: gradients and three-dimensional annular dynamics in vivo during inotropic stimulation," European Journal of Cardio-thoracic Surgery, (2001)19:431-437.

Timek, "Edge-to-Edge Mitral Valve Repair without Annuloplasty Ring in Acute Ischemic Mitral Regurgitation," [Abstract] Clinical Science, Abstracts from Scientific Sessions, 106(19):2281 (2002).

Totaro, "Mitral valve repair for isolated prolapse of the anterior leaflet: an 11-year follow-up," European Journal of Cardio-thoracic Surgery(1999) 15:119-126.

U.S. Appl. No. 60/316,892 to Tremulis et al., filed Aug. 31, 2001.

Uchida et al., "Percutaneous cardiomyotomy and valvultomy with angioscopic guidance," Am. Heart J.(1991) 121:1221-1224.

Umana et al., 'Bow-Tie' Mitral Valve Repair: An Adjuvant Technique for Ischemic Mitral Regurgitation, Ann. Thorac. Surg., May 12, 1998, pp. 1640-1646, vol. 66.

Umana et al., "'Bow-tie' Mitral Valve Repair Successfully Addresses Subvalvular Dysfunction in Ischemic Mitral Regurgitation," Surgical Forum, XLVIII:279-280 (1997).

Votta et al., "3 D computational analysis of the stress distribution on the leaflets after edge to edge repair of mitral regurgitation," Journal of Heart Valve Disease(2002)11:810 822.

Waller et al., "Anatomic Basis for and Morphologic Results from Catheter Balloon Valvuloplasty of Stenotic Mitral Valves," Clin. Cardiol. 13:655-661 (1990).

Werker, P. and Kon M., "Review of Facilitated Approaches to Vascular Anastomosis Surgery," Ann Thorac Surg 63:122-7 (1997).

U.S. Appl. No. 15/629,505 (now U.S. Pat. No. 10,945,842), filed Jun. 21, 2017 (Mar. 16, 2021).

U.S. Appl. No. 15/629,505, filed Feb. 12, 2021 Issue Fee Payment.

U.S. Appl. No. 15/629,505, filed Nov. 16, 2020 Notice of Allowance.

U.S. Appl. No. 15/629,505, filed Mar. 11, 2020 Applicant Initiated Interview Summary.

U.S. Appl. No. 15/629,505, filed Feb. 18, 2020 Request for Continued Examination (RCE).

U.S. Appl. No. 15/629,505, filed Feb. 18, 2020 Response after Final Action.

U.S. Appl. No. 15/629,505, filed Nov. 18, 2019 Final Office Action.

U.S. Appl. No. 15/629,505, filed Jul. 31, 2019 Response to Non-Final Office Action.

U.S. Appl. No. 15/629,505, filed May 2, 2019 Non-Final Office Action.

U.S. Appl. No. 15/629,505, filed Jan. 23, 2019 Response to Restriction Requirement.

U.S. Appl. No. 15/629,505, filed Nov. 29, 2018 Restriction Requirement.

* cited by examiner

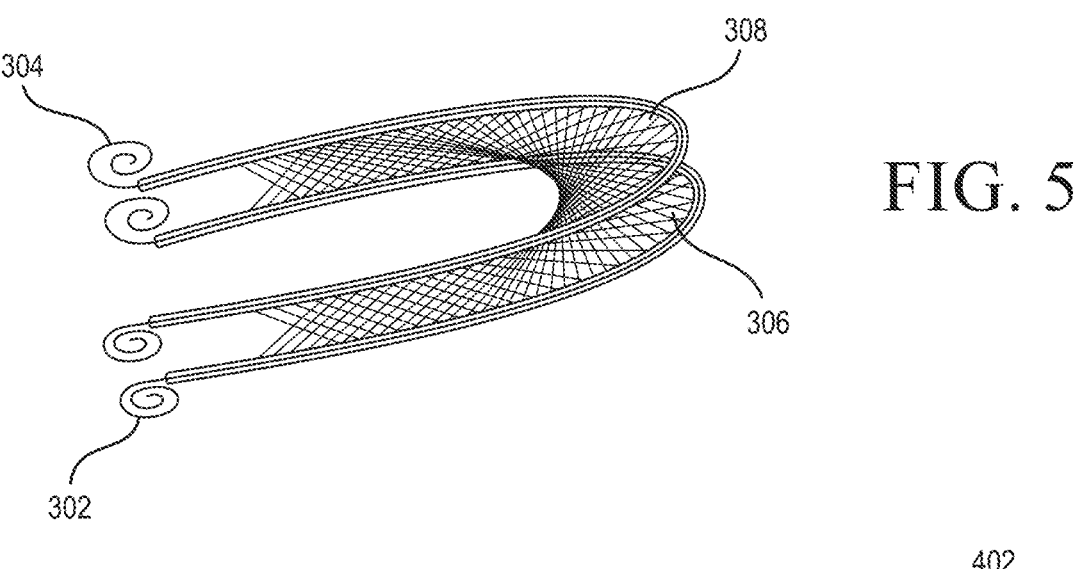
FIG. 5
FIG. 6A
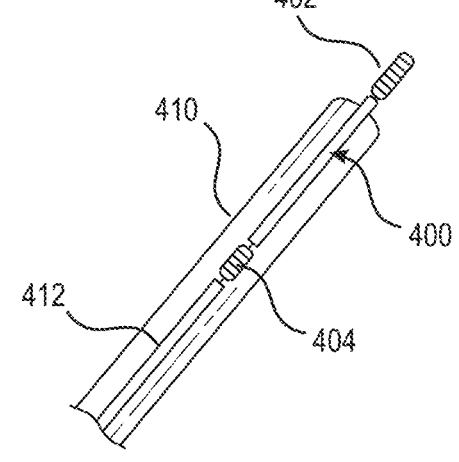
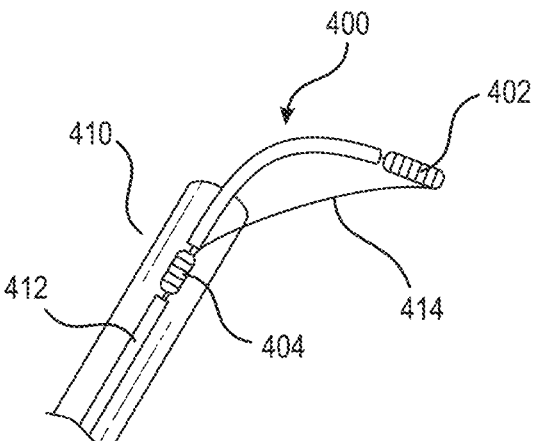
FIG. 6B

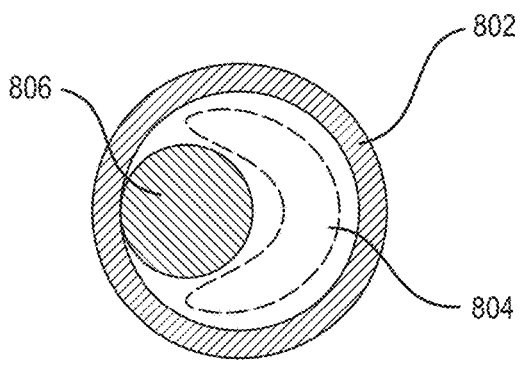
FIG. 11A
FIG. 11B
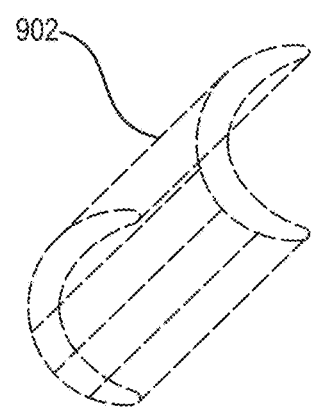
FIG. 12A
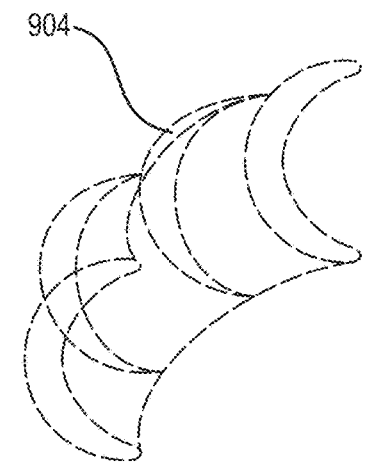
FIG. 12B
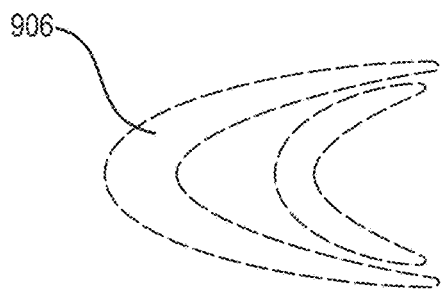
FIG. 12C
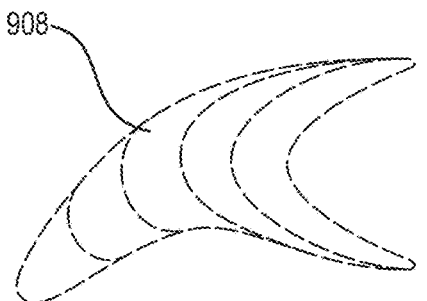
FIG. 12D

1118

1120

1100

1116

1100

1116

1122

1124

1120

ANNULAR AUGMENTATION DEVICE FOR CARDIAC VALVE REPAIR

CROSS-REFERENCE TO RELATED APPLICATIONS

This application is a continuation of U.S. patent application Ser. No. 15/629,505, filed Jun. 21, 2017, which claims priority to and the benefit of U.S. Provisional Patent Application Ser. No. 62/371,080, filed Aug. 4, 2016 and titled "ANNULAR AUGMENTATION DEVICE FOR CARDIAC VALVE REPAIR," the disclosure of which is incorporated herein by this reference in its entirety.

BACKGROUND

The mitral valve controls blood flow from the left atrium to the left ventricle of the heart, preventing blood from flowing backwards from the left ventricle into the left atrium so that it is instead forced through the aorta for distribution throughout the body. A properly functioning mitral valve opens and closes to enable blood flow in one direction. However, in some circumstances the mitral valve is unable to close properly, allowing blood to regurgitate back into the atrium. Such regurgitation can result in shortness of breath, fatigue, heart arrhythmias, and even heart failure.

A common cause of mitral valve insufficiency is functional mitral valve regurgitation (FMR). FMR typically occurs when the left ventricle of the heart is enlarged, displacing the papillary muscles that support the valve leaflets of the mitral valve and stretching the annulus (valve opening). The resulting distortion to the annulus prevents the valve leaflets from coapting together to properly close the valve, allowing blood to flow backwards across the valve.

Mitral valve regurgitation is often treated by replacing the mitral valve with a replacement valve implant or by repairing the valve through an interventional procedure. One method for repairing the mitral valve is through annuloplasty. Annuloplasty is accomplished by delivering and implanting a ring or band in the annulus of the mitral valve to attempt to return the annulus to a functioning shape.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Certain embodiments described herein are directed to devices for repairing tissue, such as a malfunctioning cardiac valve, including a regurgitant mitral valve. Some embodiments are directed to devices configured to provide repair of a regurgitant mitral valve without impeding the left ventricular outflow tract (LVOT) and/or aortic valve. For example, some embodiments are configured to enable, when deployed, proper coaptation of an anterior leaflet of a mitral valve against the device without imparting or transmitting radial forces in the septal direction which could impede, restrict, or hamper full functionality of the LVOT.

In some embodiments, a repair device includes a body having a perimeter that defines an upper side and a lower side, the perimeter having a posterior section and an anterior section. In some embodiments, the body is shaped so as to define an annular groove disposed along at least a portion of the posterior section, the annular groove being configured to receive tissue of a targeted anatomical location when the repair device is deployed at the targeted anatomical location. For example, in some implementations the annular groove is configured to receive posterior rim tissue of a targeted mitral valve.

In some embodiments, the repair device includes a first anchor and a second anchor, each anchor extending from the body in an anterior direction and configured to engage with tissue (e.g., commissure tissue of a targeted mitral valve) to prevent movement of the repair device from a targeted anatomical location when the repair device is deployed at the targeted anatomical location.

In some embodiments, the first and second anchors are substantially coplanar with the annular groove. In some embodiments, the body of the repair device is formed as a crescent-shape, with the concave side of the crescent shape defining the posterior section and the convex side of the crescent shape defining the anterior section. In some embodiments, the first anchor extends from a first intersection between the convex side and the concave side, and wherein the second anchor extends from a second intersection between the convex side and the concave side.

In some embodiments, the first anchor and/or second anchor are formed from one or more coiled or spiraled wire elements. In some embodiments, the first anchor and/or second anchor includes an upper section and a lower section (e.g., biased toward one another) to enable the gripping of tissue therebetween. In some embodiments, at least the body of the repair device includes a wire framework formed from a superelastic wire material. In some embodiments, the wire framework is incorporated with a cover or an insert.

In some embodiments, the repair device is radially outwardly biased along the posterior section and is not radially outwardly biased along the anterior section so as to prevent imparting forces to a septum of a heart when the repair device is deployed at the targeted mitral valve. In some embodiments, the body is configured in size and shape to enable an anterior leaflet of the targeted mitral valve to coapt and seal against the body.

Certain embodiments include a delivery device configured for delivery of a repair device. In some embodiments, a delivery device includes a delivery catheter having a proximal end and a distal end, a shaft disposed at least partially within the delivery catheter and configured to be translatable relative to the delivery catheter, and a repair device disposed at least partially within the delivery catheter distally from the shaft so that distal translation of the shaft and/or proximal withdrawal of the delivery catheter functions to unsheathe the repair device. In some embodiments, the repair device is housed within the delivery catheter in a collapsed configuration with at least one of the first or second anchor being positioned distally relative to the body to enable attachment of the distal anchor to targeted tissue (e.g., mitral valve commissure tissue) prior to unsheathing of the body from the delivery catheter.

Certain embodiments are directed to methods for manufacturing a repair device. In some embodiments, a method includes: forming a braid structure on a braiding mandrel; heat setting the braid structure on the braiding mandrel; removing the braid structure from the braiding mandrel; positioning the braid structure onto or into a shaping mandrel to shape the braid structure into a configuration having an annular groove and an extending section, the annular groove extending along a perimeter of a posterior section of the braid structure and the extending section extending away from the posterior section in an anterior direction; and heat setting the shaped braid structure.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 5 illustrates an alternative embodiment of a repair device;

FIGS. 6A-6B illustrate an exemplary embodiment of a delivery system configured for delivering a repair device to a targeted anatomical area within a patient's body;

FIGS. 11A and 11B illustrate cross-sectional views of shaping mandrels configured for further shaping of braid structures into shapes suitable for providing functionality as repair devices;

FIGS. 12A-12D illustrate various views of exemplary braid or wireframe structures formed using respective shaping mandrels.

DETAILED DESCRIPTION

At least some of the embodiments described herein are directed to devices for repairing a malfunctioning cardiac valve, such as a regurgitant mitral valve. Some embodiments are directed to devices configured to provide repair of a regurgitant mitral valve without impeding the LVOT (including the aortic valve). For example, some embodiments are configured to enable, when deployed, proper coaptation of an anterior leaflet of a mitral valve without imparting or transmitting radial forces in the septal direction which could impede, restrict, or hamper full functionality of the LVOT.

Although many of the examples illustrated and described herein are directed to mitral valve regurgitation, and in particular mitral valve regurgitation related to FMR, it will be understood that the principles described herein may also be applied in other applications, such as mitral valve repair having non-FMR causes, repair of other heart valves, or use in other interventional procedures or treatment applications.

Figures 1A, 1B, 1C:
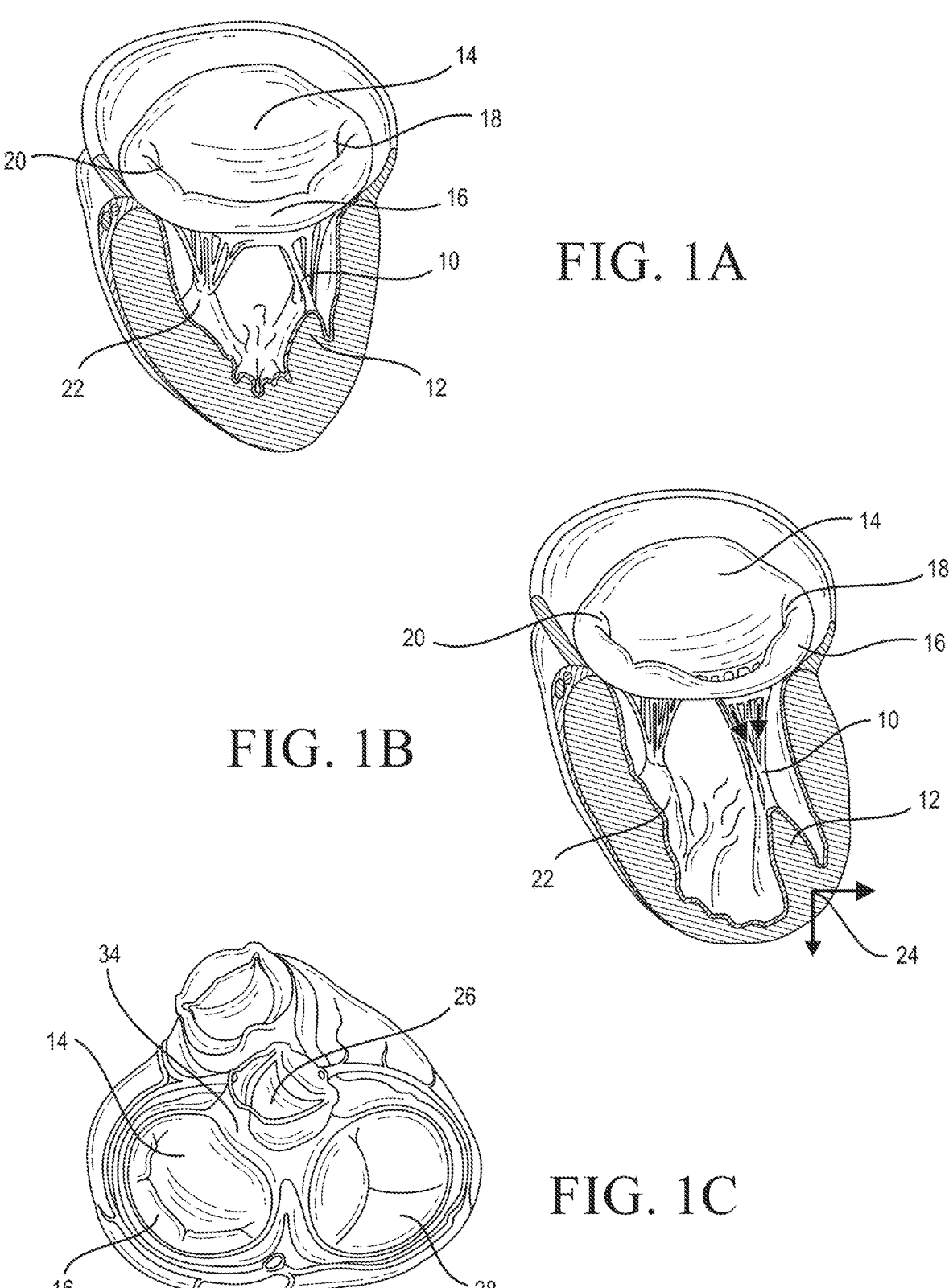
FIG. 1A illustrates a cross-sectional view of a heart with a normally functioning mitral valve.
FIG. 1B illustrates a cross-sectional view of an enlarged heart resulting in functional mitral valve regurgitation.
FIG. 1C illustrates a superior view of a heart showing the anterior leaflet 14 and posterior leaflet 16 of the mitral valve in the coapted position.

FIG. 1A illustrates a cross-sectional view of a heart showing a normal, functional mitral valve in a closed position (during ventricular systole). The mitral valve includes an anterior leaflet 14 and a posterior leaflet 16, which are attached to papillary muscles 12 and 22 by chordae tendineae 10. Although the posterior leaflet 16 has a greater circumferential length, the anterior leaflet 14 extends over a greater portion of the valve opening. The anterior leaflet 14 and posterior leaflet 16 are joined at commissures 18 and 20 (posteromedial commissure 18 and anterolateral commissure 20). The commissures 18 and 20 define an area where the anterior leaflet 14 and the posterior leaflet 16 come together at the mitral valve annulus.

FIG. 1B illustrates a cross-sectional view of a heart showing a regurgitant mitral valve as a result of FMR. As shown, the heart of FIG. 1B suffers from cardiomegaly ("enlarged heart"), which prevents adequate coaptation of the anterior leaflet 14 and posterior leaflet 16. As indicated by the arrows 24, the enlarged structure of the left ventricle pulls on the chordae tendineae 10 and prevents the leaflets 14 and 16 from properly coapting together. In the illustrated example, the posterior leaflet 16 is particularly displaced by the enlarged structure of the left ventricle. In many instances of FMR, the anterior leaflet 14 remains relatively mobile and able to contribute to sufficient leaflet coapting area, but the posterior leaflet 16 is constrained due to dilation of the annulus.

FIG. 1C illustrates a superior view of a heart showing the anterior leaflet 14 and posterior leaflet 16 of the mitral valve in the coapted position (during ventricular systole), along with the tricuspid valve 28 and open aortic valve 26. As shown, the relative positions of the aortic valve 26, the septum 34, and the mitral valve are such that radial forces from the anterior leaflet toward the septum 34 have the potential to impact the aortic valve 26 and/or other structures of the LVOT.

One regurgitant mitral valve treatment option involves implantation of a replacement mitral valve. However, replacement mitral valves are typically complex in construction and also involve complexities in delivery and deployment. For example, mitral valve replacement includes difficulties related to achieving anatomical conformity to a misshaped annulus, durability of artificial leaflets, and forming a tolerable septal crossing profile (e.g., less than about 29 Fr for acceptable femoral delivery and transeptal crossing to the left atrium without requiring subsequent septal repair). Further, the implantation of a replacement valve often requires removal or alteration of the leaflets and/or other associated structures. The inability to preserve these structures limits subsequent treatment options.

Another treatment option is annuloplasty. However, a typical annuloplasty implant, once deployed, imparts and/or allows transmittal of radial forces to the septum, which can result in compromised LVOT function. Accordingly, in many instances an annuloplasty implant may function to reduce regurgitation, but at the same time may cause or aggravate other detrimental conditions within the patient's heart.

One or more of the embodiments described herein are configured to enable repair of a regurgitant mitral valve while also avoiding one or more of the foregoing limitations of a valve replacement or typical annuloplasty procedure. For example, some embodiments are configured to enable repair of a regurgitant mitral valve without imparting or transmitting radial forces to the septum. Further, some embodiments are configured to reduce or eliminate mitral valve regurgitation while preserving leaflet and/or other valvular structures, which may be beneficial in subsequent removal, repair, or replacement procedures, or in preserving a greater number of future treatment options, for example.

Figure 2A:
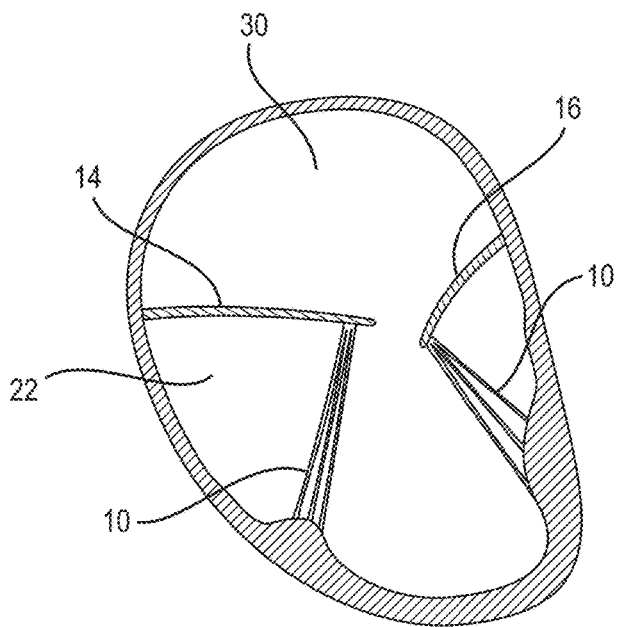
FIG. 2A illustrates a cross-sectional view of a heart with a regurgitant mitral valve prior to deployment of a repair device.
Figure 2B:
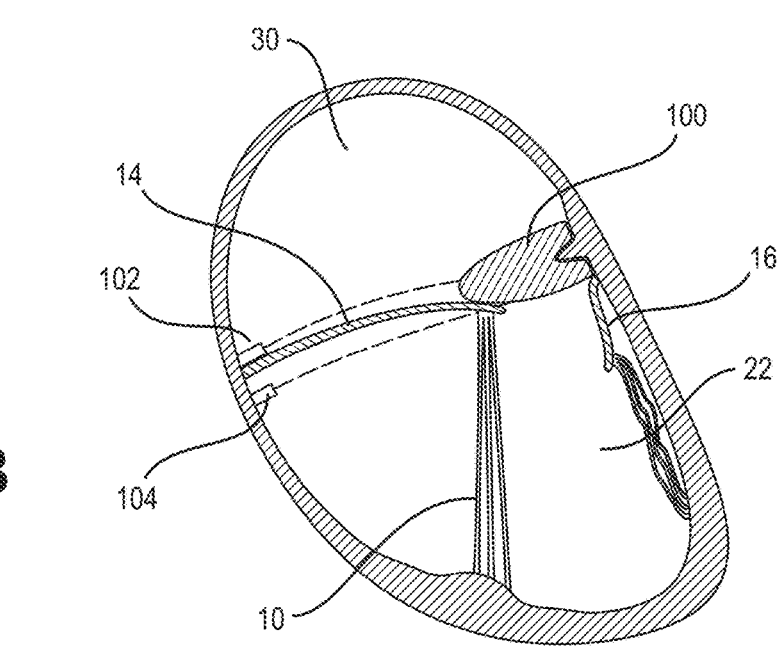
FIG. 2B illustrates a cross-sectional view of the heart of FIG. 2A after deployment of a repair device.

FIGS. 2A and 2B illustrate additional cross-sectional views of a heart with FMR, with FIG. 2A showing the heart before deployment of a repair device 100 and FIG. 2B showing the heart after deployment of the repair device 100. As shown in FIG. 2A, the posterior leaflet 16 is constrained by corresponding chordae tendineae 10 and is unable to properly coapt with the anterior leaflet 14, allowing blood to pass backward from the left ventricle 22 to the left atrium 30. FIG. 2B illustrates the repair device 100 in a deployed position on the posterior rim of the mitral valve annulus.

In some embodiments, the repair device 100 is configured to function as a static or rigid posterior leaflet, allowing the relatively more mobile anterior leaflet 14 to provide the dynamic functionality of the mitral valve. For example, because the posterior leaflet 16 extends a shorter distance across the valve (i.e., from the annulus to the leaflet margin) than the anterior leaflet 14, the implant profile of the repair device 100 may not overly restrict flow through the valve, even if the repair device 100 is configured as static or rigid. In alternative embodiments, the repair device 100 is configured with a degree of flexibility to enable dynamic movement that more closely resembles natural movement of the posterior leaflet 16.

As shown, the repair device 100 is positioned to extend across the mitral valve toward the anterior leaflet 14 a distance sufficient to allow the anterior leaflet 14 to close against the repair device 100 and prevent regurgitation during ventricular systole. As explained in more detail below, the repair device 100 includes anchors 102 and 104 which, when the repair device is deployed, are positioned within corresponding commissures of the mitral valve. In some embodiments, the anchors 102 and 104 are positioned so as to stabilize and support the repair device in the deployed position while minimizing or preventing septal directed forces of the repair device 100.

Figures 3A, 3B, 3C:
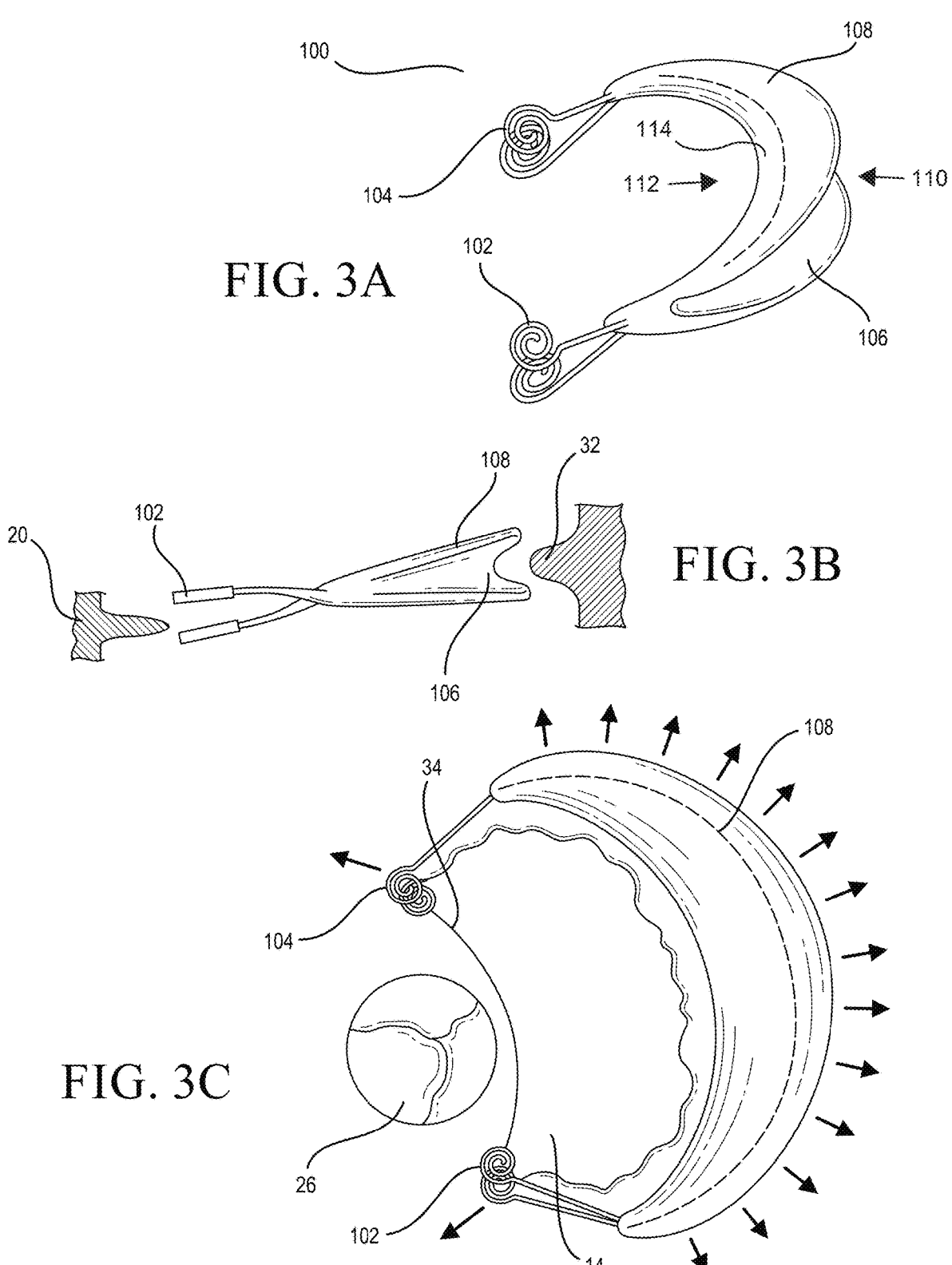
FIGS. 3A-3C illustrate various views of an exemplary embodiment of a repair device.

FIGS. 3A-3C illustrate various views of the exemplary repair device 100. FIG. 3A illustrates an isometric view of the repair device 100, showing a crescent-shaped body 108 of the device and the anchors 102 and 104 extending from the body 108 in an anterior direction. In the illustrated embodiment, the body 108 is formed so as to define a groove 106 disposed along a posterior section 110 of the body 108. The body 108 includes an anterior section 112 opposite the posterior section 110, the anterior section 112 having a coaptation surface 114 configured to coapt with an anterior leaflet of a native mitral valve. As shown, the repair device 100 is structured so that when deployed, the repair device 100 does not need to conform or attach to the entirety of the annular circumference of the mitral valve annulus. Rather, as best shown in the side view of FIG. 3B, the illustrated repair device 100 is able to be deployed along the posterior rim 32 of the annulus.

In the illustrated embodiment, the groove 106 allows the repair device 100 to be deployed and registered against the posterior rim 32, while the anchor 102 allows attachment to the commissure 20 (and the opposite anchor allows attachment to the opposite commissure). In some embodiments, the groove 106 and/or anchors 102 and 104 operate to prevent upward or downward movement of the device 100 into the atrium or ventricle once it has been deployed. For example, as shown in the illustrated embodiment, the anchors 102 and 104 and/or the groove 106 provide both atrial-side and ventricular-side engagement of annular tissue to prevent atrial and ventricular migration of the device. In some embodiments, the groove 106 also reduces or prevents the occurrence of paravalvular leakage (e.g., leakage between the repair device and the posterior rim) during ventricular systole.

FIG. 3C illustrates a superior view of the repair device 100 in a deployed position showing that the anterior leaflet 14 is able to close against the body 108 of the repair device. The anchors 102 and 104 are positioned at the commissures (not shown). As illustrated, the repair device 100 is configured so that when deployed, forces are imparted radially against the posterior rim of the annulus, but not radially against the septum 34. For example, when deployed, the repair device 100 will be outwardly radially biased along the posterior section; however, the structure of the repair device 100 prevents any outward radial forces extending from the anterior section of the device 100. This configuration and distribution of forces beneficially minimizes or avoids imparting pressure across the septum 34 and to the aortic valve 26 or other structures of the LVOT. In addition, in at least some implementations, the illustrated configuration minimizes or eliminates any detrimental effect to the functioning of the anterior leaflet 14.

In some embodiments, the anchors 102 and 104 and/or other components of a repair device are formed from a superelastic material, such as a nickel-titanium alloy. When deployed, the anchors 102 and 104 are preferably configured to flex to reduce tissue damage and/or necrosis. In some embodiments, the anchors 102 and 104 and/or other components of a repair device are treated to reduce the likelihood of thrombus formation and/or encourage tissue ingrowth and endothelialization. For example, one or more components of a repair device may be coated with a mesh covering (e.g., a polyester woven sock) or other tissue growth promoter to encourage tissue ingrowth. Additionally, or alternatively, the anchors 102 and 104 and/or other components of a repair device may be coated with a biocompatible film and/or other surface treatment.

In some embodiments, the anchors 102 and 104 are formed from a superelastic nickel-titanium alloy or other superelastic material, and the remainder of the repair device is formed from a biocompatible polymer, such as one or more of an ultra-high molecular weight polyethylene (UHMWPE), polyether ether ketone (PEEK), polyester, or a flexible biogel. Preferably, at least the body 108 of the repair device 100 is formed from a material that minimizes metallic interference with magnetic resonance imaging (MRI), computed tomography (CT) scanning, fluoroscopy, or other imaging technique. In some embodiments, one or more struts are passed through the body 108 to provide structure to the repair device 100. For example, a wire framework may support a cover and/or insert to form the device 100. In some embodiments, superelastic wire material utilized to form one or more of the anchors may pass through the body 108 of the repair device to form a wire framework that may be covered or coupled with an insert formed from a separate polymer material or other suitable biocompatible material.

FIGS. 4A-4D illustrate various configurations of an anchor 202 that may be utilized in one or more of the repair device embodiments described herein for attachment to a commissure 20. Preferred anchor configurations include curved and/or castellated structures to increase surface contact and reduce point pressure on tissue once deployed. In the illustrated embodiments, the anchors 202 include upper and lower (e.g., atrial and ventricular) sections for engaging opposite sides of a commissure 20 when deployed. In some embodiments, the opposite sides are configured to be biased toward one another to provide a holding force for engaging a commissure when deployed.

Figures 4A, 4B, 4C, 4D:
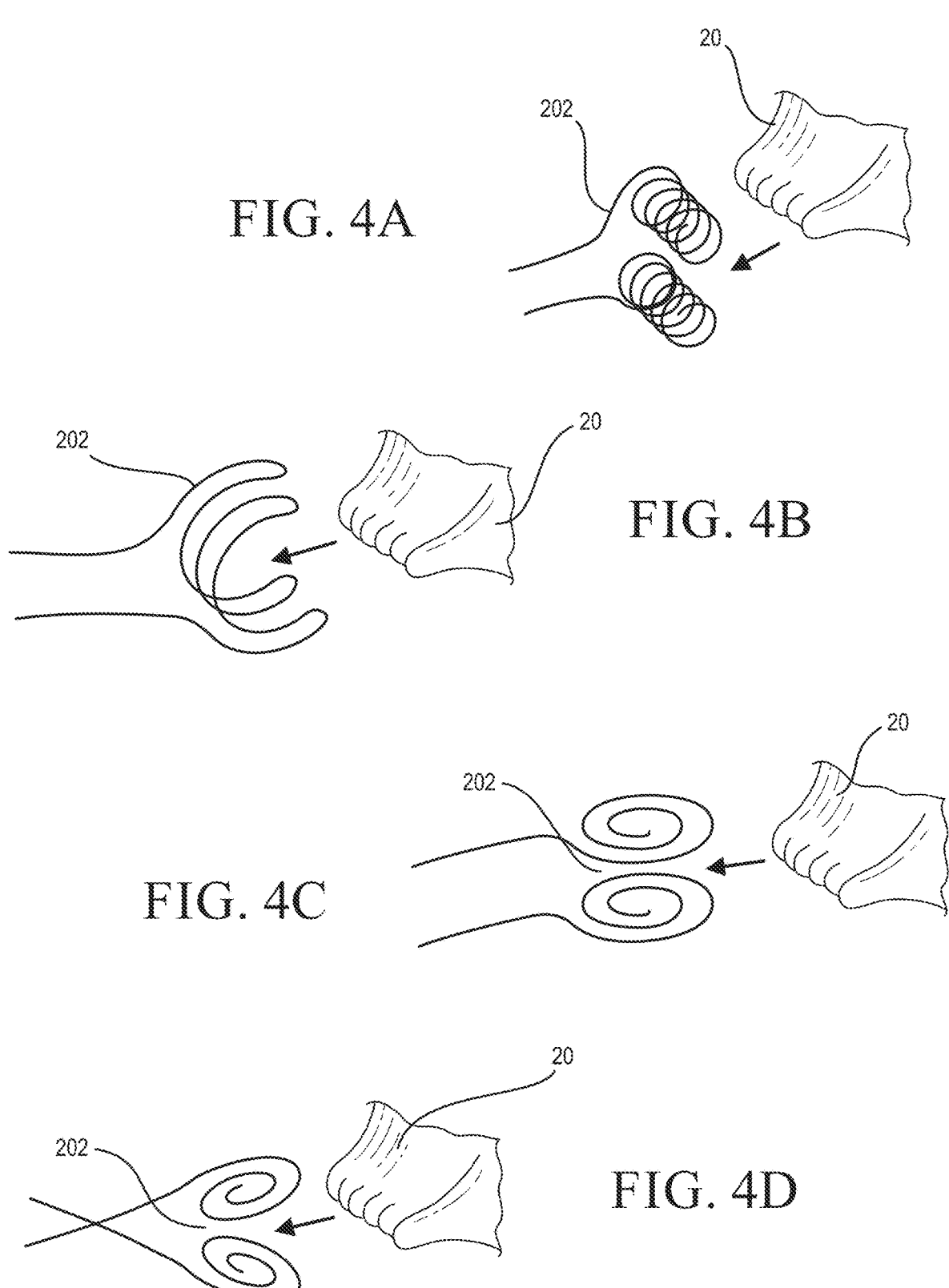
FIGS. 4A-4D illustrate various exemplary configurations of an anchor of a repair device.

The illustrated anchors 202 are formed as wires shaped to provide an anchor configuration. For example, wires (e.g., nickel-titanium alloy wires) can be shaped to form one or more of circles, spirals, loops, and the like. As shown, a pair of opposing wires may be utilized to form upper and lower (e.g., atrial and ventricular) sections. In some embodiments, one or more wires may be structured to form an arrangement of vertically oriented coils, as shown in FIG. 4A. In some embodiments, one or more wires may be arranged to form a crescent-shaped structure, as shown in FIG. 4B. In some embodiments, one or more wires may be arranged to form a horizontally oriented spiral, as shown in FIGS. 4C and 4D.

In some embodiments, one or more anchors include one or more barbs, hooks, tines, or other fixing structures configured to enhance fixation of the anchor to the commissure tissue when deployed and to increase resistance to dislodging of the anchor caused by hemodynamic forces across the valve. Additionally, or alternatively, one or more anchors may include an enhanced surface area or roughened surface texture adapted to increase tissue grip and resistance to dislodging.

FIG. 5 illustrates an alternative embodiment of a repair device including a body 308 shaped so as to define a posterior facing groove 308 and anchors 302 and 304 extending in an anterior direction from the body 308. The illustrated embodiment is configured as a set of opposing crescent-shaped wires joined by a woven and/or mesh covering material or webbing extending between the opposing wires. When deployed, a first wire would be disposed on the atrial side of the posterior rim of the annulus while a second wire would be disposed on the ventricular side of the posterior rim of the annulus, with the covering material extending across and abutting against the posterior rim. In some embodiments, this configuration beneficially provides one or more of effective tissue ingrowth, minimized posterior dilation of the repaired valve, and low-profile construction which enables non-invasive delivery (e.g., transfemoral). In some embodiments, the shape may be delivered in a closed or collapsed configuration which opens to an open or expanded configuration during deployment. Exemplary methods and systems related to delivery and deployment of a repair device are described in more detail below.

One or more components of the illustrated embodiment may have variable thickness to provide desired structure and/or strength. For example, the anchor regions 302 and 304 may be provided with more structure and strength relative to the webbing. Additionally, or alternatively, variable gauges of wire may be used in a forming process so as to manage the profile (collapsed and/or expanded) of the repair device while imparting strength where needed (e.g., the anchor and/or annulus regions of the device). The illustrated embodiment is shown as a shaped wireframe structure. In other embodiments, a repair device may have a half-stent construction, such as formed by cutting (e.g., laser cutting) stent tubing to form the repair device shape as illustrated.

The sections of the repair device which are contacted against the posterior rim of the annulus when the device is deployed (e.g., the sections within the groove 306) are preferably porous and/or surface treated so as to encourage tissue ingrowth. The surfaces contacting the anterior leaflet and functioning to obstruct regurgitation (e.g., the non-groove sections of the body 308) are preferably non-porous and/or smooth to enable obstruction of regurgitant flow while minimizing effects on functioning of the anterior leaflet.

An alternative embodiment of a repair device includes one or more components formed from a porous polymer (e.g., formed from a foam-like polymer material). For example, such a repair device may be delivered to a targeted valve in a compressed and low profile configuration, and then upon deployment and saturation with blood, the repair device opens to an expanded configuration. Additionally, or alternatively, a repair device may include one or more fillable chambers that may be filled, for example, with saline, a biogel, or a curable resin. By way of example, a repair device may be delivered in a compressed configuration. During or after deployment, the one or more chambers may then be filled to at least partially open the device toward an expanded configuration. Such embodiments are preferably formed from a material that resists hemodynamic flow through the material (e.g., during ventricular systole) and allows coaptation with the anterior leaflet.

In some embodiments, a repair device includes a body having a solid structure. In alternative embodiments, a repair device includes a body formed as a wireframe structure that may be covered by or integrated with a covering. Additional examples of repair device structures are described in more detail below.

FIGS. 6A and 6B illustrate an example repair device delivery system including a repair device 400 with anchors 402 and 404, the repair device 400 being housed within a delivery catheter 410. The repair device 400 may represent any of the repair device embodiments described herein. The illustrated embodiment includes a shaft 412 which may be abut or be coupled to a proximal end of the repair device 400 (e.g., at anchor 404) and housed within the delivery catheter 410 along with the repair device 400. The shaft 412 and delivery catheter 410 are translatable relative to one another such that the repair device 400 may be unsheathed from the distal end of the delivery catheter by distal pushing of the shaft 412 relative to the delivery catheter 410 and/or proximal withdrawal of the delivery catheter 410 relative to the shaft 412.

In the illustrated embodiment, the anchor 402 is positioned at the distal end of the repair device 400. In one exemplary implementation, the repair device 400 may be partially unsheathed from the delivery catheter 410 so as to expose the distal anchor 402, resulting in the configuration shown in FIG. 6A. the distal anchor 402 may be directed to a commissure of the targeted valve (e.g., the posteromedial commissure) to engage with the commissure. The repair device 400 may then be further unsheathed from the delivery catheter 410 so as to expose the body of the repair device 400 for engagement with the posterior rim of the mitral valve. In preferred embodiments, the repair device 400 has sufficient rigidity to remain secured against the annulus while the remainder of the repair device 400 is unsheathed from the delivery catheter 410.

Further unsheathing reveals the proximal anchor 404, which is directed to the remaining commissure (e.g., the anterolateral commissure) to engage with the commissure. In some embodiments, one or more of the anchors 402 and 404 are formed from a shape memory material such that they conform to a three-dimensional shape to capture and/or engage with the respective commissures upon being unsheathed from the delivery catheter 410.

In some embodiments, the length of the repair device is sized prior to delivery and deployment of the device. For example, a repair device may be sized for a particular patient based on imaging or other factors. In other embodiments, the size of the repair device is adjustable. For example, one or more of the anchors may be translatable along at least a portion of the length of the repair device in a ratcheting or "zip-tie" fashion.

FIG. 6B illustrates a configuration of the repair device delivery system including a control wire 414 attached at or near the distal end of the repair device 400 and passing proximally through the delivery catheter 410 to a control handle (not shown). Tensioning of the control wire 414 enables steering of the distal end of the repair device 400 toward its anatomical target (e.g., one of the commissures). The control wire 414 may be formed as a braided polymer or monofilament, for example. One or more control wires may be routed internally within the delivery catheter 410, such as within grooves or lumens of the delivery catheter 410, such that when tensioned, the one or more control wires do not consume outboard space and/or interfere with anatomic structures.

Figures 7A, 7B, 7C:
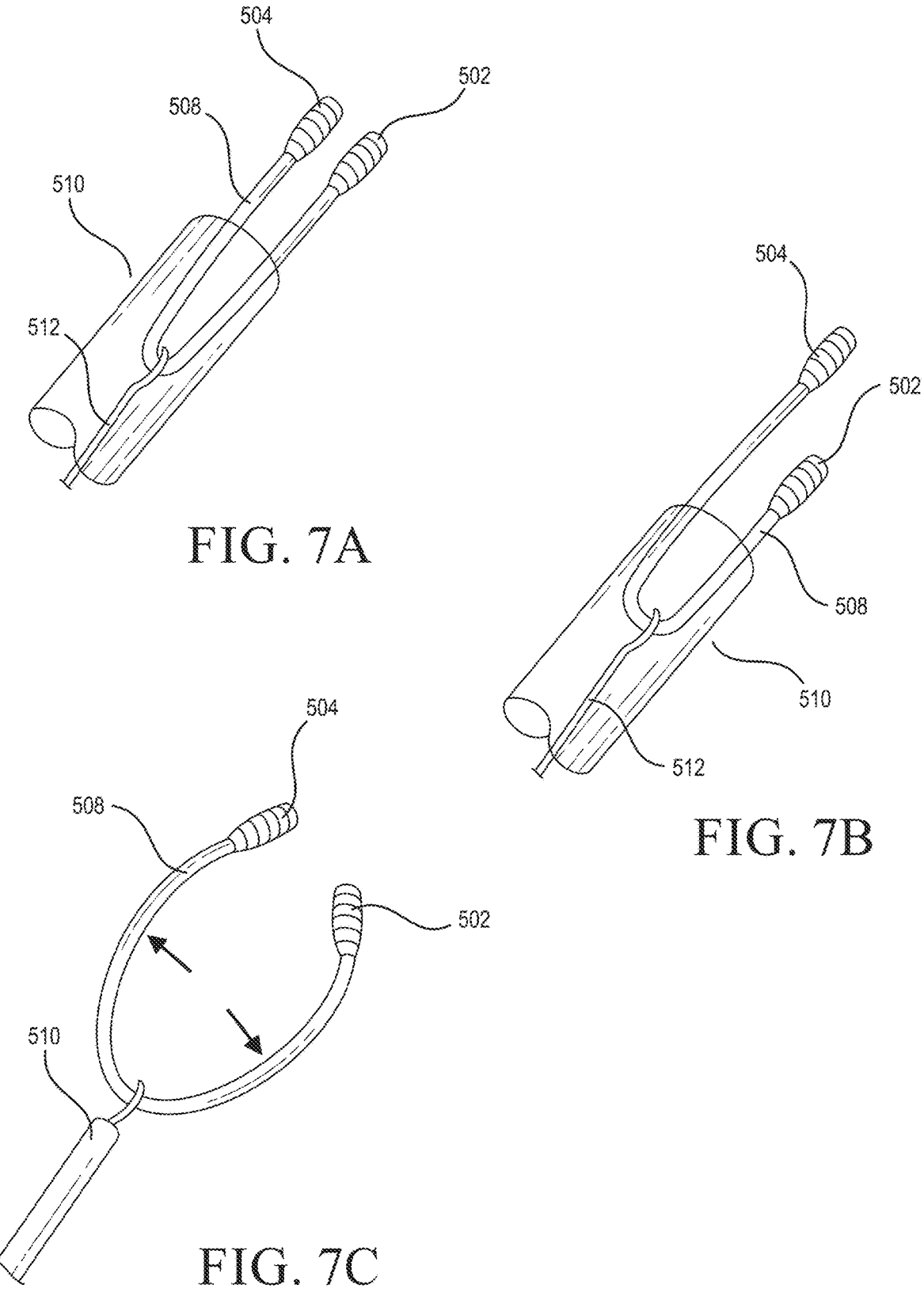
FIGS. 7A-7C illustrate an alternative embodiment of a delivery system configured for delivering a repair device to a targeted anatomical area within a patient's body.

FIGS. 7A-7C illustrate another embodiment of a repair device delivery system for delivery of a repair device having a body 508 and anchors 502 and 504. The illustrated embodiment includes a delivery catheter 510 and a rod 512 disposed radially within the delivery catheter 510 and configured to be translatable relative to the delivery catheter 512. As shown, the rod 512 is coupled to the body 508 of the repair device so as to enable the repair device to be unsheathed from the delivery catheter 510 by pushing the rod 512 distally relative to the delivery catheter 510 and/or withdrawing the delivery catheter 510 proximally relative to the rod 512. In the illustrated embodiment, the rod 512 includes a hooked end for engaging around the body 508 of the repair device. In other embodiments, a rod may omit a hook so as to function as a push structure, or may be detachably adhered, magnetically coupled, and/or mechanically fastened to the repair device, for example.

The configuration shown in FIG. 7A positions the anchors 502 and 504 substantially equally from the rod 512. FIG. 7B shows an alternative configuration where the anchors 502 and 504 are positioned in an offset fashion, with the anchor 504 being positioned further distally from the rod 512 than the anchor 502. Such an offset configuration may enable a lower overall profile for the repair device when positioned within the delivery catheter 510. FIG. 7C illustrates deployment of the repair device from the delivery catheter 510. In the illustrated embodiment, the body 508 of the repair device moves toward an expanded configuration when unsheathed from the delivery catheter 510. The body 508 and/or other components of the repair device may be formed from a shape-memory material that provides such functionality to the repair device.

The embodiment shown in FIGS. 7A-7C is configured with the anchors 502 and 504 of the repair device positioned distally relative to the body 508, such that the anchors 502 and 504 are unsheathed before the remainder of the body 508 of the repair device. Such an embodiment beneficially allows the anchors 502 and 504 to be attached to respective commissures prior to fully unsheathing the body 508 of the repair device and unfolding or expanding of the repair device. However, in other embodiments, a repair device may be oriented within a delivery catheter with anchors positioned proximally relative to the body of the repair device, such that at least a portion of the body is unsheathed from the delivery catheter prior to the anchors being unsheathed.

The embodiment shown in FIGS. 7A-7C beneficially enables delivery of a repair device from a position or orientation that is transverse to the mitral valve plane. For example, transeptal delivery of the delivery catheter 510 may result in the distal end of the delivery catheter being oriented transverse to the mitral valve plane. Steering and positioning of the repair device (e.g., elevation, axial rotation, pitch) may be adjusted by manipulating the rod 512. After lodging the anchors 502 and 504 in their respective commissures, manipulation of the rod 512 relative to the delivery catheter 510 enables the body 508 of the repair device to be properly positioned/oriented for deployment against the posterior annular rim of the mitral valve.

Other delivery methods may also be utilized. For example, a repair device may be delivered surgically or transapically. In one example of a transapical approach, a repair device is introduced through the apex of the left ventricle wall and brought to the valve plane before deployment.

Embodiments described herein may be formed with a lower profile and lower bending stiffness than a conventional valve replacement device. The relatively small profile and low bending stiffness provide beneficial utility as compared to such conventional valve replacement procedures. Reductions in complications related to arrhythmias and/or LVOT obstruction may be provided by the devices, systems, and methods described herein. Further, such devices are relatively easy to orient and properly position.

In some embodiments, particularly those intended for transcatheter delivery, one or more radiopaque markers may be included at various locations of the device. Such marker may be placed on the device to identify orientation details with respect to how the device is positioned in the mitral valve. In one embodiment, a marker is placed at a midseptum section of the device to aid the user in registering device orientation.

FIGS. 8 through 12D illustrate various process steps directed to the manufacture of a repair device as described herein. One or more of the illustrated and described steps may be utilized to manufacture, at least in part, one or more of the repair device embodiments described herein. In one exemplary method, a repair device is manufactured by: forming a braid structure on a braiding mandrel; heat setting the braid structure on the braiding mandrel; positioning the braid structure onto or into a shaping mandrel to shape the braid structure into a configuration having an annular groove and an extending section, wherein the annular groove extends along a perimeter of a posterior section of the braid structure and the extending section extends away from the posterior section in an anterior direction such that the annular groove is configured to accommodate a posterior annular rim of a mitral valve and the extending section is configured to accommodate coaptation of an anterior leaflet against the extending section; and heat setting the braid structure. Some embodiments may further include one or more of laser welding sections of the structure(s) together, passivating and/or electro-polishing the finished braid structures, attaching an insert and/or cover to the braid structure, and loading the braid structure into a delivery catheter to form a repair device delivery system.

Figure 8:
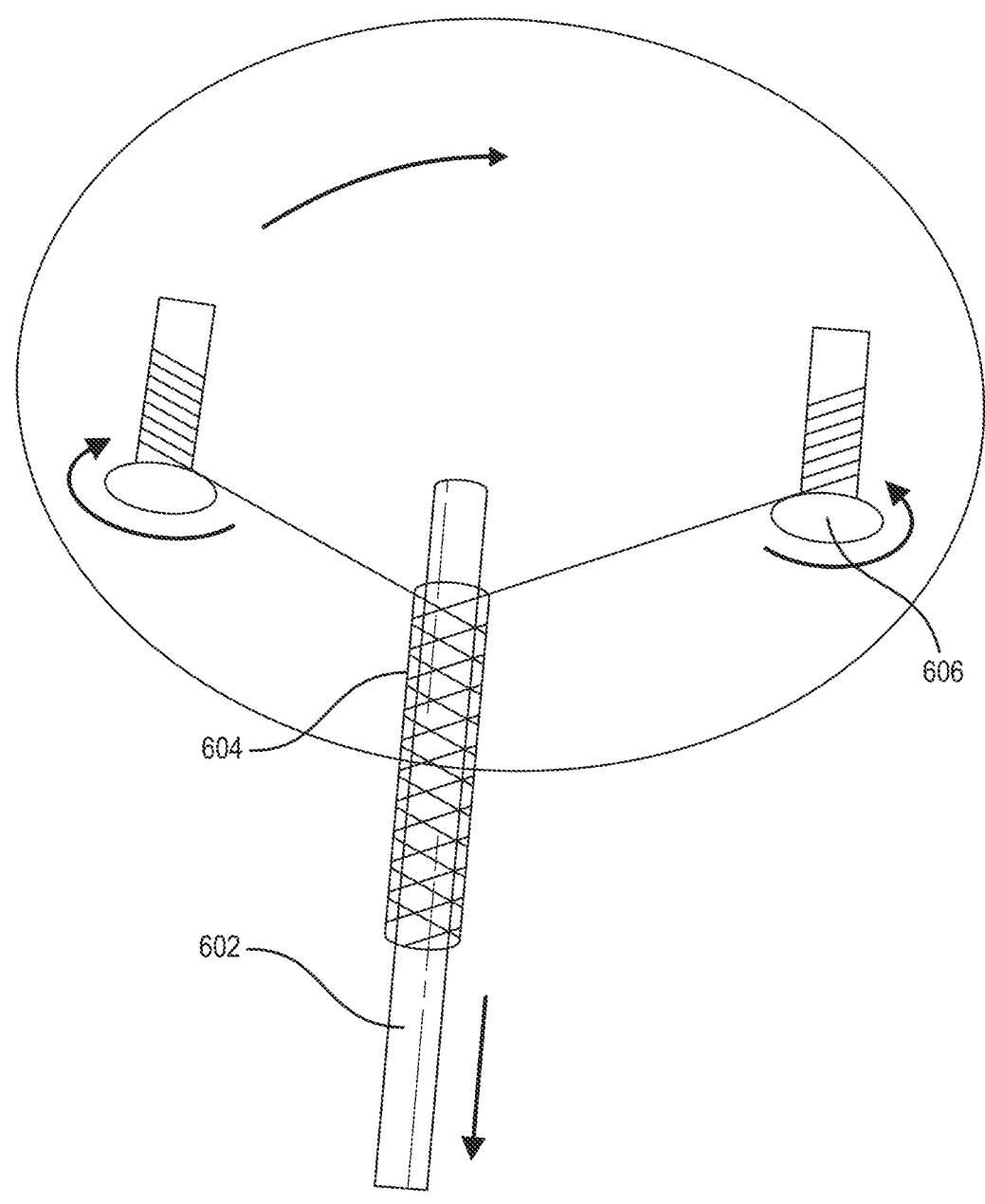
FIG. 8 illustrates the formation of a braid structure on a mandrel as part of an exemplary process for manufacturing a repair device.

FIG. 8 illustrates a manufacturing device that may be used as at least part of a process for manufacturing a repair device, such as one or more of the repair device embodiments described herein. In the illustrated embodiment, a braid structure 604 is formed by wrapping wire around a mandrel 602 as the mandrel 602 is displaced relative to one or more spool components 606. The illustrated mandrel 602 has a cylindrical shape. Other embodiments may include mandrels having alternative shapes, such as tapering cylinders, tapering or non-tapering ovoid cross-sectional shapes, tapering or non-tapering polygonal cross-sectional shapes, and shapes having a wing-like cross-section matching the geometry of a posterior leaflet, for example. Wires used to form the braid structure 604 may be formed from a superelastic material, such as a suitable nickel titanium alloy. Other embodiments may utilize wire formed from other metals, alloys, or polymers.

Wires used to construct various sections of the device may have different cross sections to reduce the overall profile of the device when collapsed into the delivery catheter and/or to provide strength to the anchoring features. One or more wires may also include undulations and/or other non-linear features to improve intra-strut interactions, strength, and/or to reduce profile. Various manufacturing steps are described in more detail below.

In some embodiments, after a braid structure 604 has been formed, the free ends are back-braided, welded, adhered, or otherwise incorporated into the body of the braid structure 604. The braid structure 604 may then be heat set (e.g., at about 500 to 550 degrees C. for about 15-20 minutes) while still being held on the mandrel 602. For example, in some embodiments, the braid structure 604 is formed from a shape memory material, such as a nickel titanium alloy having shape memory properties.

Figure 9A:
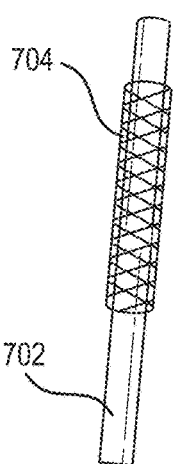
FIGS. 9A-9C illustrate various exemplary mandrel shapes.
Figure 9B:
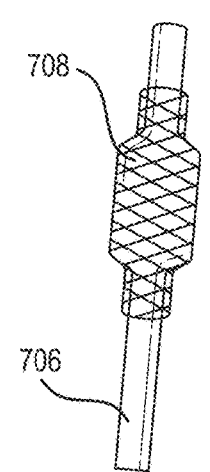
Figure 9C:
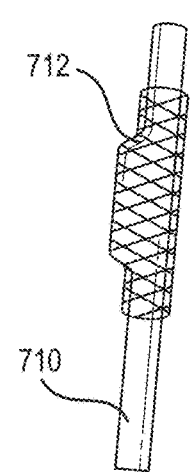
Figure 10A:
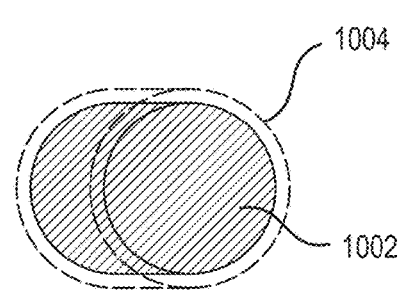
FIGS. 10A-10D illustrate cross-sectional views of various exemplary braid structure shapes formed on corresponding mandrels.
Figure 10B:
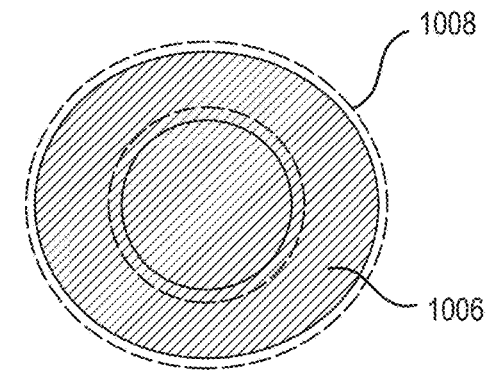
Figure 10C:
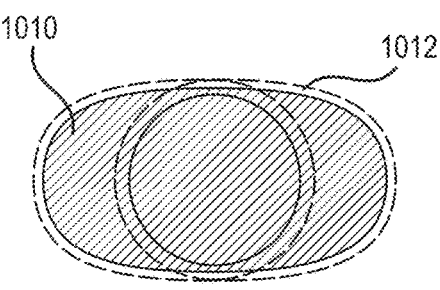
Figure 10D:
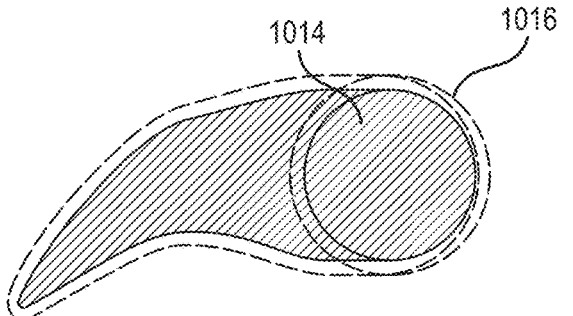

FIGS. 9A-9C illustrate various mandrels 702, 706, and 710 having different shapes to form different respective braid structures 704, 708, and 712. FIGS. 10A-10D illustrate cross-sectional views of various mandrels 1002, 1006, 1010, and 1014 having different shapes to form different respective braid structures 1004, 1008, 1012, and 1016. For example, FIG. 10A illustrates a mandrel 1002 having an eccentric tubular cross-sectional shape, FIG. 10B illustrates a mandrel 1006 having a coaxially tapered tubular shape, FIG. 10C illustrates a mandrel 1010 having a cross-sectional shape that transitions from circular to ovoid, and FIG. 10D illustrates a mandrel 1014 having a wing-like cross-sectional shape similar to a posterior leaflet profile shape.

In some embodiments, after heat setting of a braid structure onto a braiding mandrel, the braid structure is removed from the mandrel (e.g., using split tubes for some part geometries, as needed) and placed onto or into a shaping mandrel for further shaping of the braid structure. FIGS. 11A and 11B illustrate, in cross-sectional view, placement of braid structures 804 and 810 into shaping mandrels 802 and 808, respectively. In the illustrated embodiment, the shaping mandrels 802 and 808 are formed as hollow cavity mandrels to constrain and shape the outer periphery sections of the respective braid structures 804 and 810. The illustrated shaping mandrels 802 and 808 also include respective shaping rods 806 and 812 for further defining and shaping of the periphery sections of the braid structures 804 and 810.

The illustrated embodiments form braid structures 804 and 810 having a generally V-shaped cross section for providing an annular groove structure and an extending section. For example, one or more shaping rods may be utilized to form an annular groove shape enabling engagement of a resulting repair device with commissure tissue and/or posterior annular rim tissue upon deployment of the repair device. In addition, an extending section enables a resulting repair device to provide a coapting surface against which an anterior leaflet may close once the repair device has been deployed in a targeted mitral valve.

The embodiment shown in FIG. 11A has a non-tapering profile, while the embodiment shown in FIG. 11B has a tapering profile. After shaping of a braid structure in a shaping mandrel, the braid structure may be subjected to heat setting to set the final shape of the braid structure. The heat setting parameters may be as described above (e.g., about 500 to 550 degrees C. for about 15 to 20 minutes for nickel-titanium alloy based embodiments) or other suitable combination of temperature and time to provide desired shape setting of the shape-memory material of the braid structure (e.g. a particular time and temperature combination suitable for the particular type of shape memory material used).

FIGS. 12A-12D illustrate views of various braid structures 902, 904, 906, and 908 that may be formed using a shaping mandrel as described by the foregoing. For example, FIG. 12A illustrates a braid structure 902 having a crescent-shaped cross section, FIG. 12B illustrates a braid structure 904 having a crescent-shaped cross section and an axially curved profile, FIG. 12C illustrates a braid structure 906 having a progressively tapering profile, and FIG. 12D illustrates a braid structure 908 having a wing like cross section similar to a posterior leaflet profile shape.

In some embodiments, a braid structure may be finished by electro-polishing and/or passivation (e.g., using HF or $HNO_3$ acid, or other suitable acid). In some embodiments, a braid structure may be fitted with a covering and/or insert. For example, in embodiments where the braid density is low, a covering and/or insert may be added to enable the repair device to function to block regurgitant flow. A covering or insert may be formed from polyester, other polymer, or other suitable biocompatible material. In embodiments with sufficient braid density (e.g., sufficient to provide acceptable blockage of regurgitant flow, a covering and/or insert may be omitted.

In some embodiments, to prepare a repair device for loading onto or into a delivery device, the repair device may be stretched to an elongated and lower profile shape, cooled (e.g., using a liquid nitrogen spray and/or another suitable coolant and/or cooling process), and collapsed (e.g., through reversible martensitic deformation) into a delivery device, such as a delivery sheath or delivery catheter. In some embodiments, a funnel may be utilized to enable the repair device to be collapsed and directed into the delivery device.

Figures 13A, 13B, 13C:
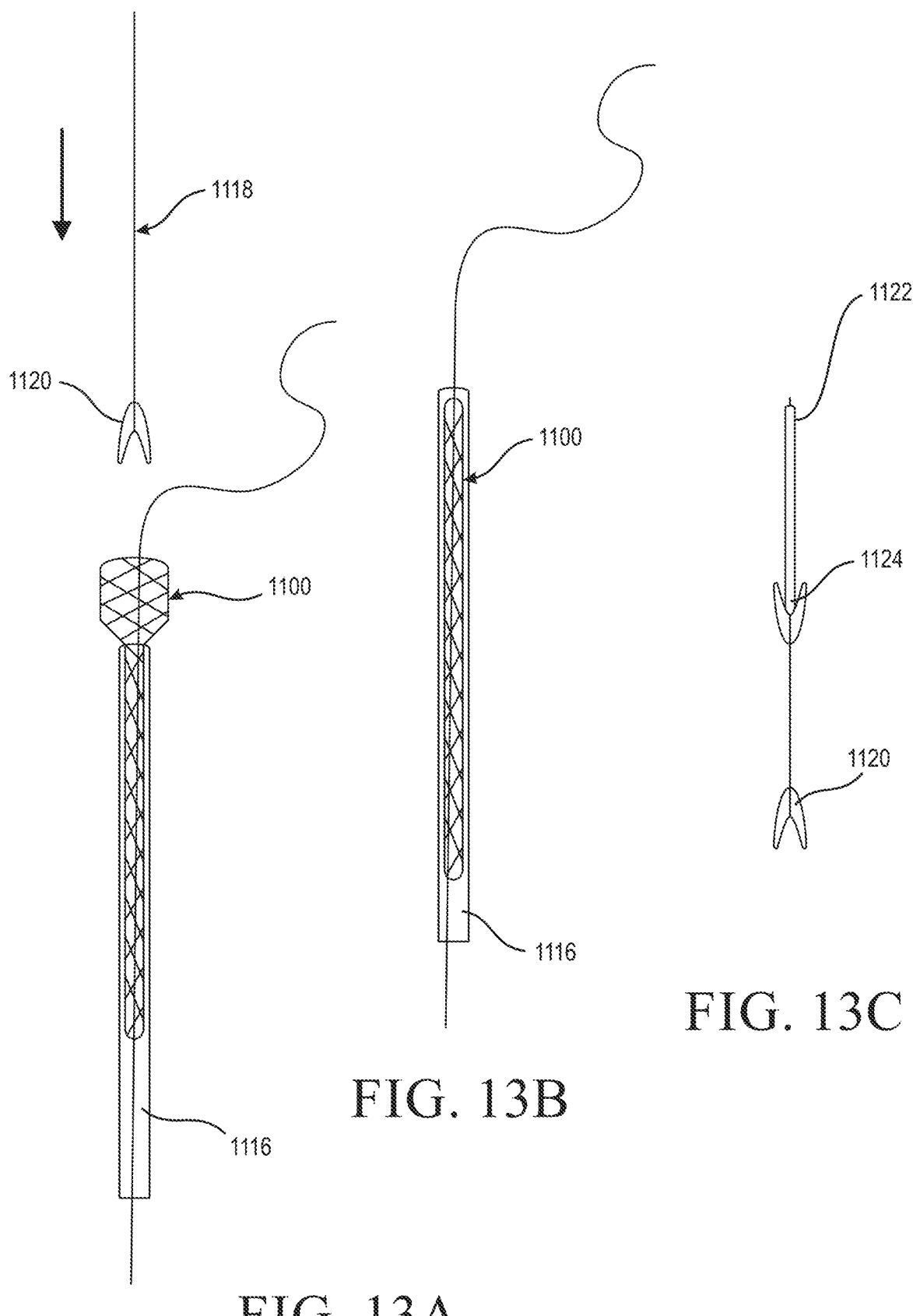
FIGS. 13A-13C illustrate the loading of a braid or wireframe structure into a delivery catheter as part of an exemplary loading process.

FIGS. 13A-13C illustrate an embodiment of a loading process for loading a repair device 1100 into a delivery catheter 1116 using a ratchet 118. In the illustrated embodiment, the ratchet 118 includes a clasp 1120 for engaging with the repair device 1100 to enable pushing of the repair device 1100 into the delivery catheter 1116 via pushing of the ratchet 1118. For example, the clasp 1120 may be configured to catch one or more wires/struts of the repair device 1100 to provide engagement with the repair device.

FIG. 13A illustrates the braid structure of the repair device 1100 partially positioned within the delivery catheter 1116, and FIG. 13B illustrates the repair device after being fully directed into the delivery catheter 1116. In some embodiments, the ratchet 1118 may remain in the delivery catheter 11116 to function as a pushing tool or pushing rod for the resulting delivery system.

FIG. 13C illustrates another embodiment of a ratchet 1122 having both a forward clasp 1120 for pushing a repair device, and a reverse clasp 1124 for engaging with one or more wires/struts of a repair device to enable the repair device to be pulled backwards and/or retracted through a delivery catheter.

As used herein, the term "vertical" refers to an orientation that is substantially perpendicular to a plane defined by a mitral valve annulus of a heart. As used herein, the term "horizontal" refers to an orientation that is substantially parallel to the plane defined by the mitral valve annulus of the heart.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Elements described in relation to any embodiment depicted and/or described herein may be combinable with elements described in relation to any other embodiment depicted and/or described herein. For example, any element described in relation to a repair device of FIGS. 2B to 5 may be combinable with any element described in relation to a repair device delivery system of FIGS. 6A to 7C, unless clearly described otherwise.

The present invention may be embodied in other forms, without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of repairing tissue at a native mitral valve, the method comprising:

transfemorally delivering a repair device proximate the native mitral valve, wherein the repair device includes:

a body comprising an anterior section and a posterior section, the body being crescent-shaped with the concave side of the crescent-shaped body defining the posterior section and the convex side of the crescent-shaped body defining the anterior section, the anterior section having a coaptation surface configured to coapt with an anterior leaflet of the native mitral valve on a side of the body opposite the concave side, the posterior section having a concave surface shaped to receive tissue of a posterior rim of an annulus of the native mitral valve, and an anchor extending anteriorly from the body, wherein the anchor is substantially coplanar with the concave surface, wherein the body and the anchor together have a collapsed configuration for transfemoral delivery and an expanded configuration upon deployment; and deploying the repair device proximate to the native mitral valve to engage tissue proximate to an anterior portion of the native mitral valve with the anchor to anchor the posterior section of the body against the posterior rim of the annulus of the native mitral valve such that the posterior rim of the annulus is received by the concave surface of the posterior section of the body, wherein the coaptation surface is disposed on a side of the body opposite the concave surface such that when the posterior rim is received by the concave surface, the coaptation surface is positioned to coapt with the anterior leaflet at the annulus of the native mitral valve.

2. The method of claim 1, wherein the anchor includes an upper anchor section and a lower anchor section.

3. The method of claim 1, wherein the anchor includes at least one barb.

4. The method of claim 3, wherein the at least one barb is configured to enhance fixation of the anchor to tissue.

5. The method of claim 1, wherein the anchor is configured to allow movement of an anterior leaflet of the native mitral valve when the anchor is engaged with tissue proximate the anterior portion of the native mitral valve.

6. The method of claim 1, wherein the anchor is configured to stabilize the body against the posterior portion of the native mitral valve while minimizing septal directed forces when engaged with tissue proximate the anchor portion of the native mitral valve.

7. The method of claim 1, wherein at least the body comprises a wire framework.

8. The method of claim 7, wherein the wire framework is formed from a superelastic wire material.

9. The method of claim 1, wherein the body is configured to enable an anterior leaflet of the native mitral valve to coapt against the body when anchored at the native mitral valve.

10. The method of claim 1, further comprising a tissue growth promoter disposed on at least a portion of the repair device to encourage tissue growth.

11. The method of claim 1, wherein at least the body is formed of an expandable polymer.

12. The method of claim 1, wherein deploying the repair device includes positioning the crescent-shaped body such that it imparts radial forces against the posterior rim of the annulus without imparting radial forces against a septum.

13. The method of claim 12, wherein the concave surface forms a groove along the posterior section, and wherein deploying the repair device includes engaging the posterior rim with the groove to provide both atrial-side and ventricular-side engagement of the posterior rim to prevent atrial and ventricular migration of the repair device.

14. The method of claim 13, further comprising reducing paravalvular leakage between the repair device and the posterior rim during ventricular systole via the groove receiving the posterior rim.

15. The method of claim 1, wherein the repair device includes two anchors extending anteriorly from the body, and wherein deploying the repair device includes positioning the two anchors at commissures of the native mitral valve.

16. The method of claim 1, wherein deploying the repair device includes positioning the body such that an anterior leaflet of the native mitral valve can close against the anterior section of the body.

17. The method of claim 16, further comprising allowing the anterior leaflet to coapt against the anterior section of the body during systole.

18. The method of claim 1, wherein deploying the repair device includes positioning the body such that it does not conform to or attach to an entirety of an annular circumference of the mitral valve annulus.

19. A method of repairing tissue at a native mitral valve, the method comprising:

transfemorally delivering a repair device proximate the native mitral valve, wherein the repair device includes:

a body comprising an anterior section and a posterior section, the body being crescent-shaped with the concave side of the crescent-shaped body defining the posterior section and the convex side of the crescent-shaped body defining the anterior section, the anterior section having a coaptation surface configured to coapt with an anterior leaflet of the native mitral valve on a side of the body opposite the concave side, the posterior section having a concave surface shaped to receive tissue of a posterior rim of an annulus of the native mitral valve, and an anchor extending anteriorly from the body, wherein the anchor is substantially coplanar with the concave surface, wherein the body and the anchor together have a collapsed configuration for transfemoral delivery and an expanded configuration upon deployment; and deploying the repair device proximate to the native mitral valve to engage tissue proximate to an anterior portion of the native mitral valve with the anchor to anchor the posterior section of the body against the posterior rim of the annulus of the native mitral valve such that the posterior rim of the annulus is received by the concave surface of the posterior section of the body, wherein the coaptation surface and the concave surface are positioned within a valve plane of the native mitral valve.

* * * * *